(12) United States Patent
Saeki et al.

(10) Patent No.: US 9,138,185 B2
(45) Date of Patent: Sep. 22, 2015

(54) LANCET ASSEMBLY AND PRICKING DEVICE

(71) Applicants: IZUMI-COSMO COMPANY, LIMITED, Osaka (JP); ASAHI POLYSLIDER COMPANY, LIMITED, Osaka (JP)

(72) Inventors: Hideaki Saeki, Okayama (JP); Hirokazu Imori, Okayama (JP); Kazuharu Seki, Tokyo (JP)

(73) Assignees: IZUMI-COSMO COMPANY, LIMITED, Osaka (JP); ASAHI POLYSLIDER COMPANY, LIMITED, Osaka (JP)

( * ) Notice: Subject to any disclaimer, the term of this patent is extended or adjusted under 35 U.S.C. 154(b) by 205 days.

(21) Appl. No.: 13/718,179

(22) Filed: Dec. 18, 2012

(65) Prior Publication Data

US 2013/0204162 A1 Aug. 8, 2013

(30) Foreign Application Priority Data

Dec. 20, 2011 (JP) ................. P2011-278465

(51) Int. Cl.
*A61B 5/151* (2006.01)
*A61B 5/15* (2006.01)

(52) U.S. Cl.
CPC .......... *A61B 5/150564* (2013.01); *A61B 5/1411* (2013.01); *A61B 5/15019* (2013.01); *A61B 5/1519* (2013.01); *A61B 5/150022* (2013.01); *A61B 5/15113* (2013.01); *A61B 5/15115* (2013.01); *A61B 5/15117* (2013.01); *A61B 5/15188* (2013.01); *A61B 5/15194* (2013.01); *A61B 5/150412* (2013.01); *A61B 5/150618* (2013.01); *A61B 5/150709* (2013.01); *A61B 5/150725* (2013.01); *A61B 5/150893* (2013.01); *A61B 5/150908* (2013.01); *A61B 5/150259* (2013.01); *A61B 5/150786* (2013.01)

(58) Field of Classification Search
CPC ............ A61B 5/15142; A61B 5/1411; A61B 5/1422; A61B 5/150725; A61B 5/150801; A61B 5/150893; A61B 5/150374; A61B 5/150434; A61B 5/150541; A61B 5/150641; A61B 5/150571
USPC ................................. 600/583; 606/181, 182
See application file for complete search history.

(56) References Cited

U.S. PATENT DOCUMENTS

| | | | | |
|---|---|---|---|---|
| 5,324,303 | A * | 6/1994 | Strong et al. ................. | 606/181 |
| 5,385,571 | A | 1/1995 | Morita | |
| 8,133,246 | B1 * | 3/2012 | Starnes ........................ | 606/182 |
| 8,246,645 | B2 * | 8/2012 | Yoritaka et al. .............. | 600/583 |
| 2007/0225742 | A1 * | 9/2007 | Abe et al. ..................... | 606/182 |
| 2008/0058847 | A1 * | 3/2008 | Abe et al. ..................... | 606/181 |
| 2009/0275969 | A1 * | 11/2009 | Kitamura et al. ............. | 606/182 |
| 2009/0299398 | A1 * | 12/2009 | Yoritaka et al. .............. | 606/182 |

* cited by examiner

*Primary Examiner* — Devin Henson
*Assistant Examiner* — David J McCrosky
(74) *Attorney, Agent, or Firm* — Wenderoth, Lind & Ponack, L.L.P.

(57) ABSTRACT

A lancet assembly includes a lancet, a lancet engaging part, and a lancet case housing the lancet and the lancet engaging part. In the lancet assembly of the present invention, the lancet engaging part and the lancet cap are disposed such that they are capable of making contact with each other. When the lancet engaging part is forced to move forward with respect to the lancet in a pricking direction, the lancet cap is pressed by the lancet engaging part, and thereby the bridging component is broken so that the lancet cap is separated from the lancet body. When the lancet engaging part is forced to further move forward, the separated lancet cap moves to the position off a pricking pathway of the pricking component within the lancet case.

14 Claims, 29 Drawing Sheets

Cap in a separated state (at a point in time when engagement of lancet body and case is released.)

Fig. 1
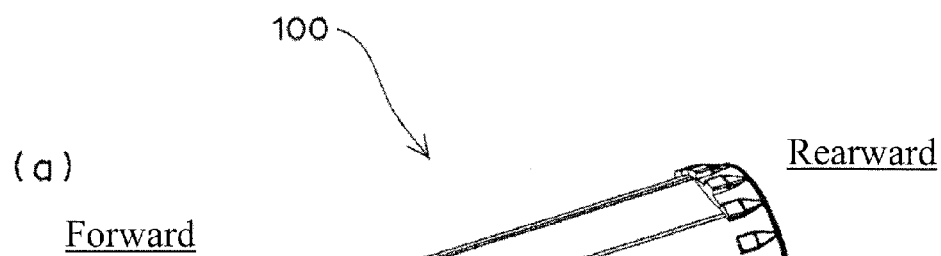
(a)  Forward  Rearward
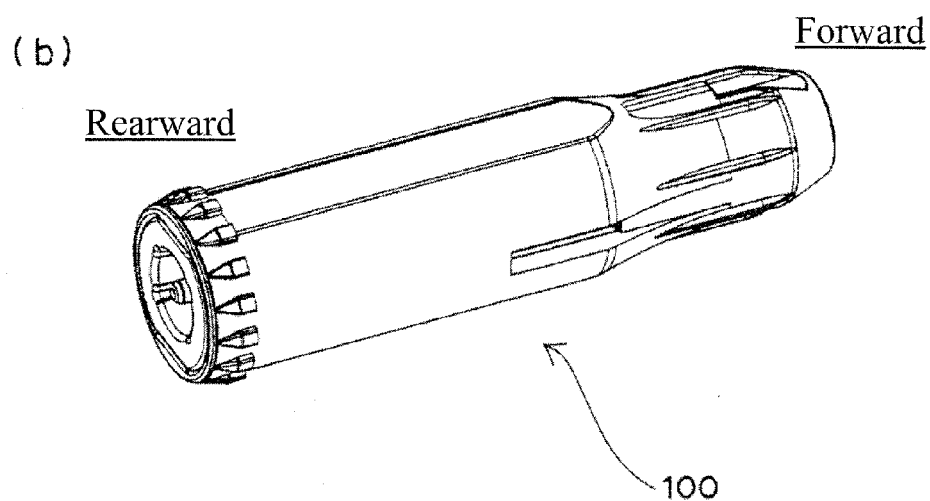
(b)  Rearward  Forward

Fig. 6
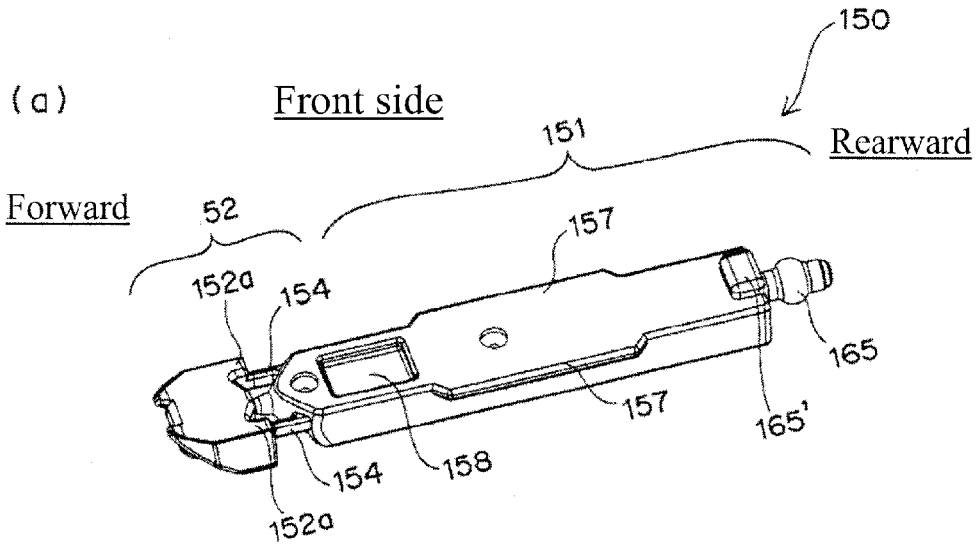
(a) Front side
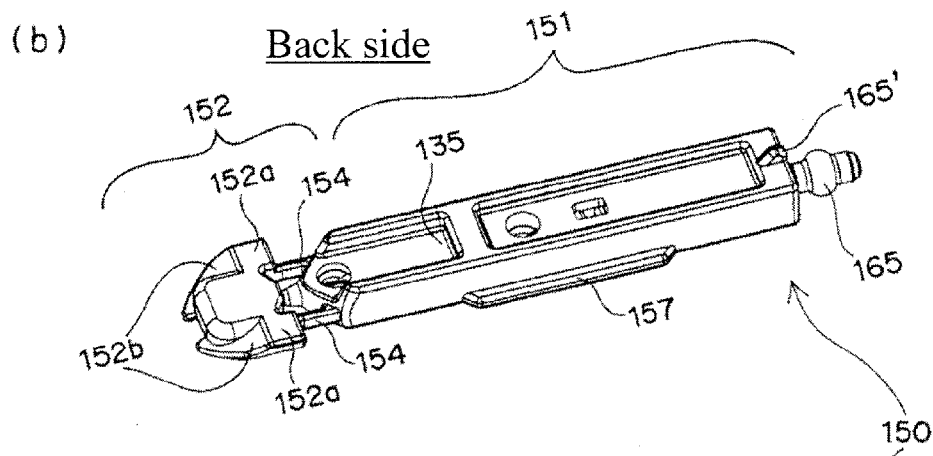
(b) Back side
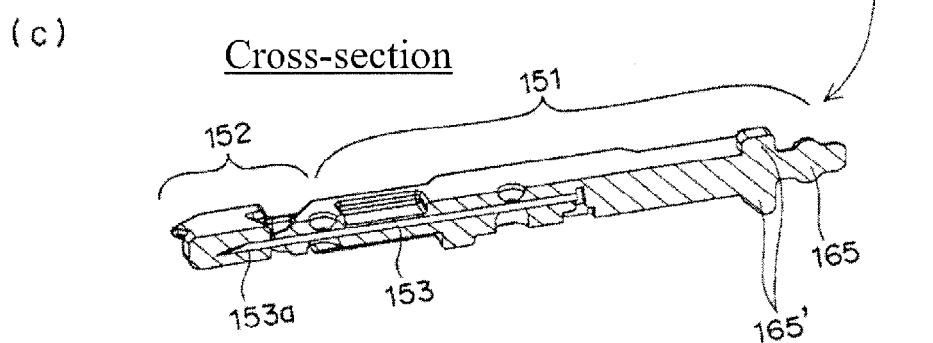
(c) Cross-section

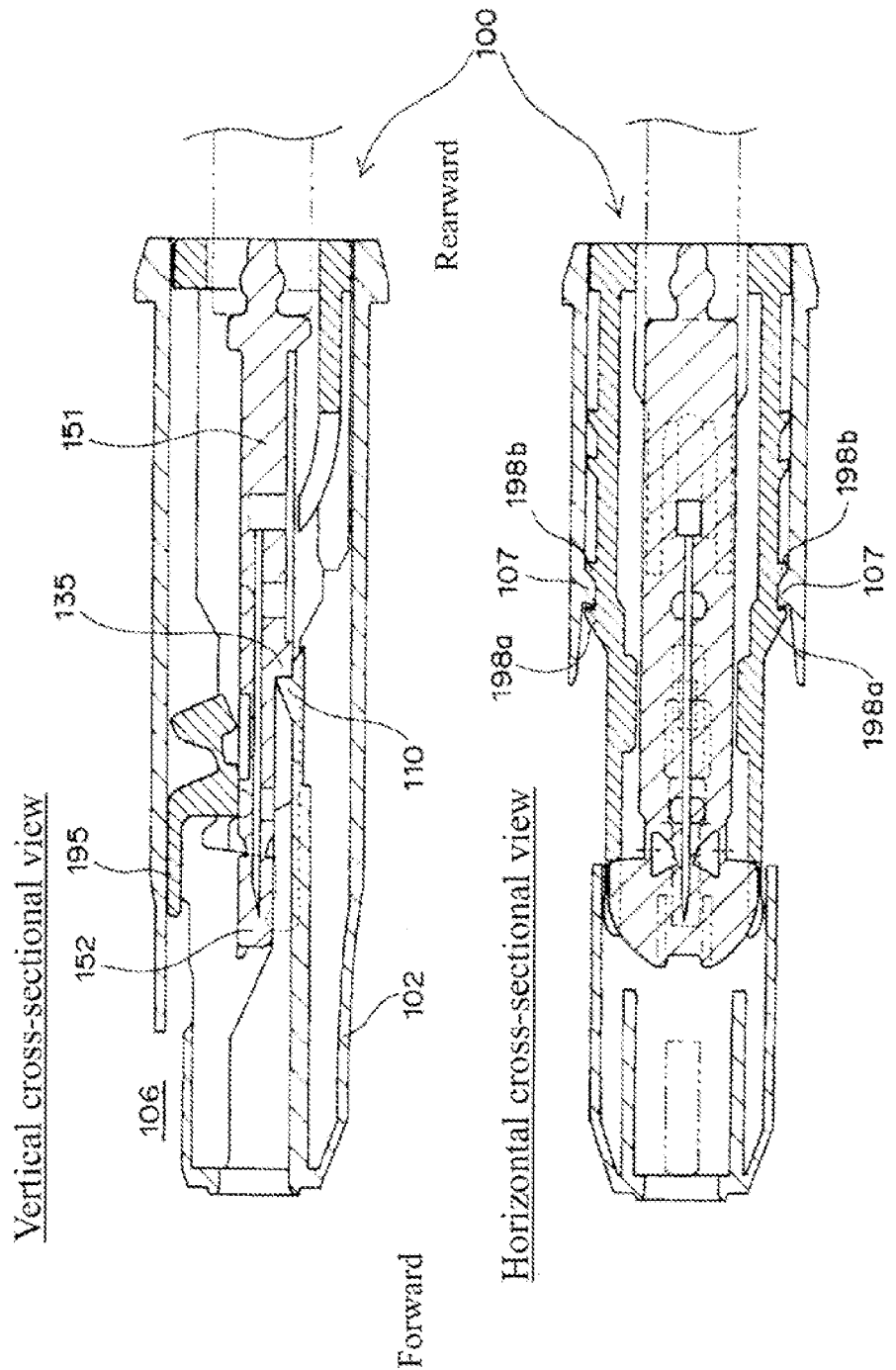

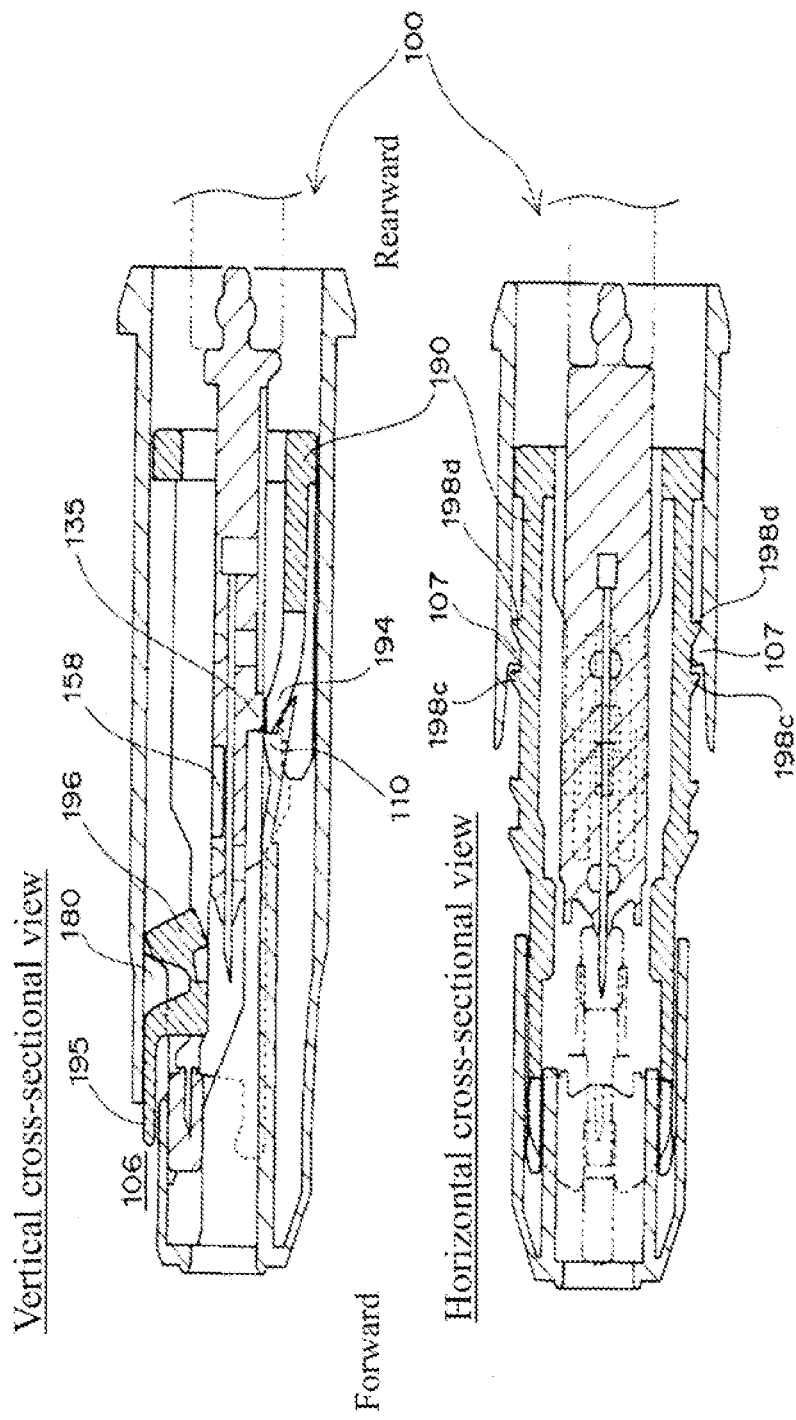

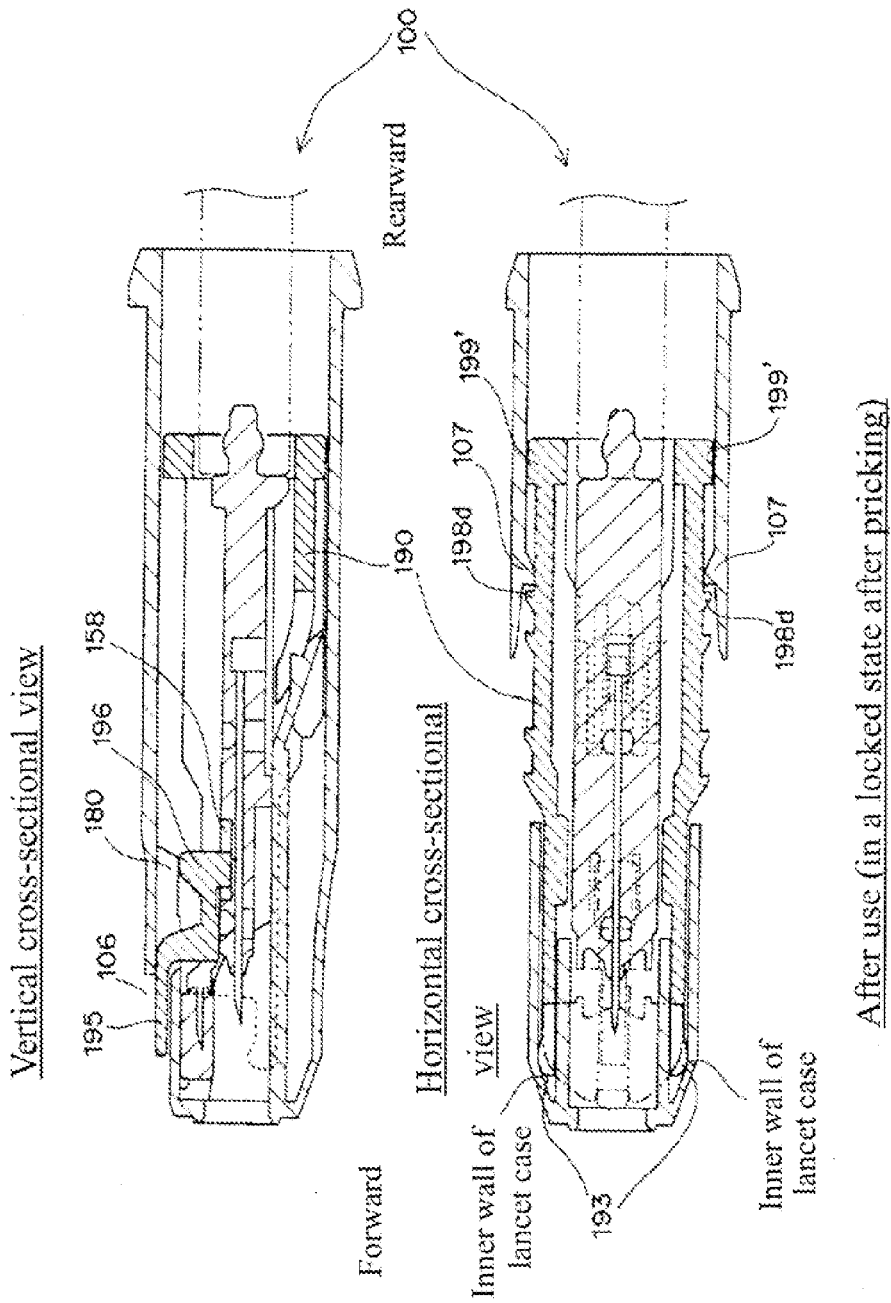

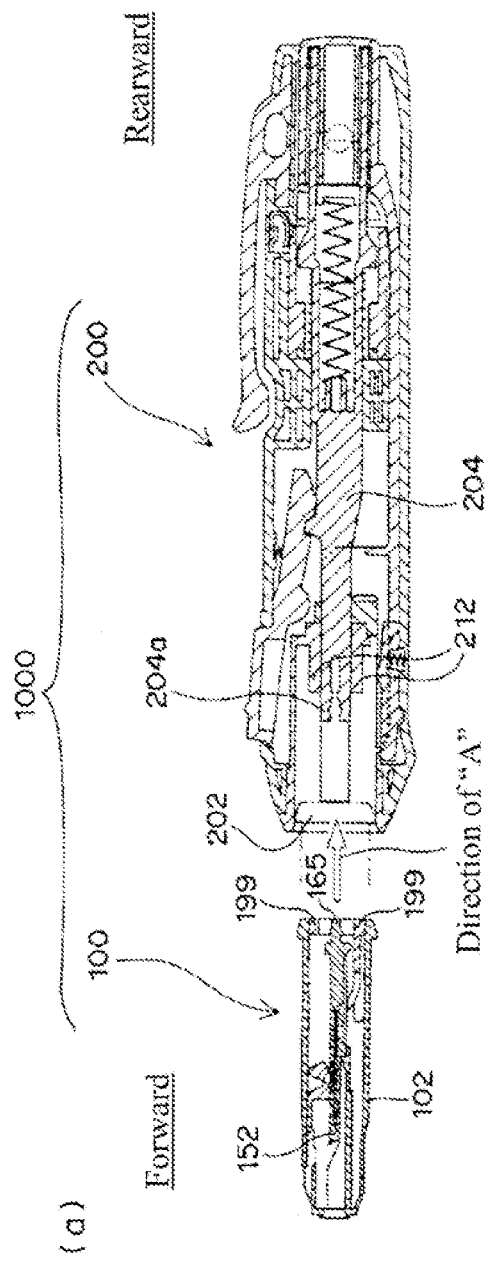
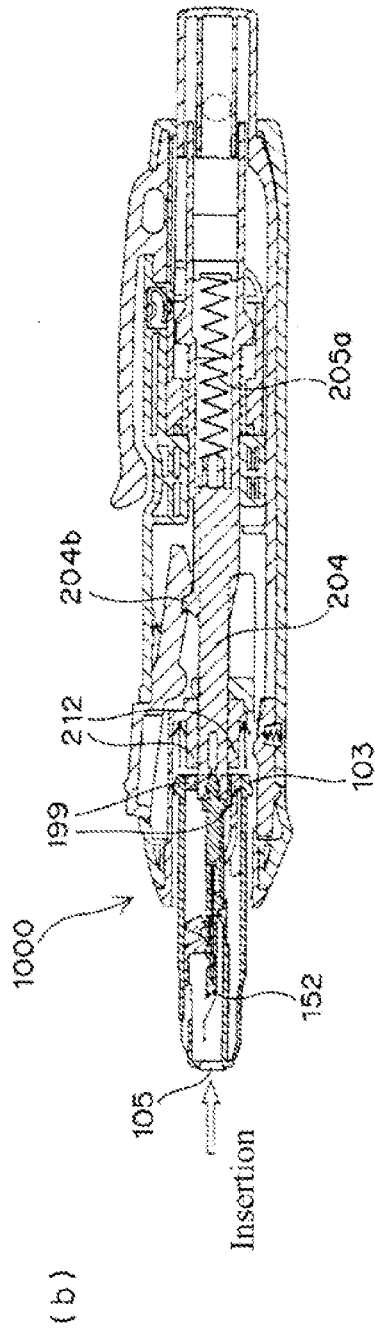
Fig. 9A

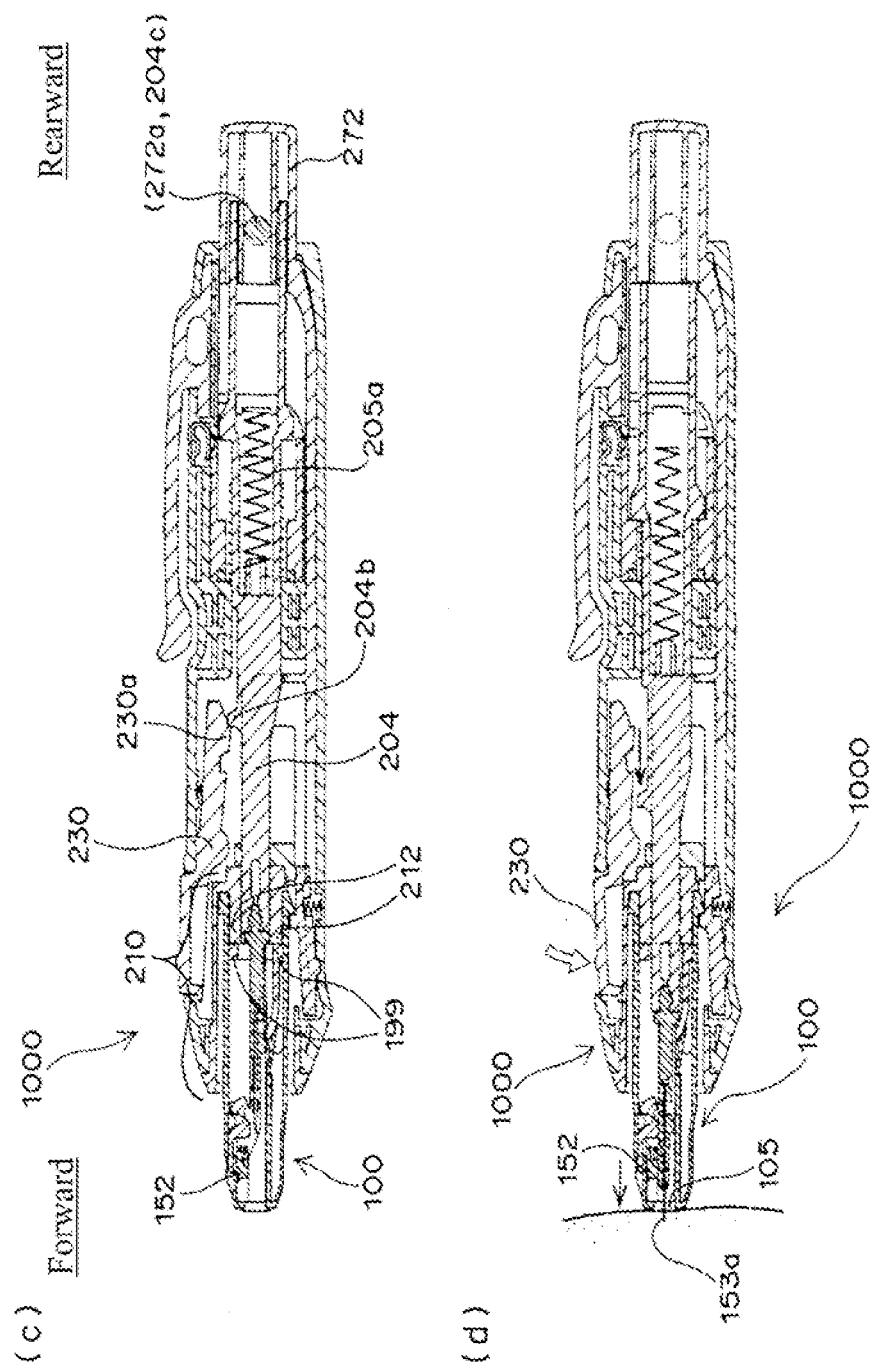

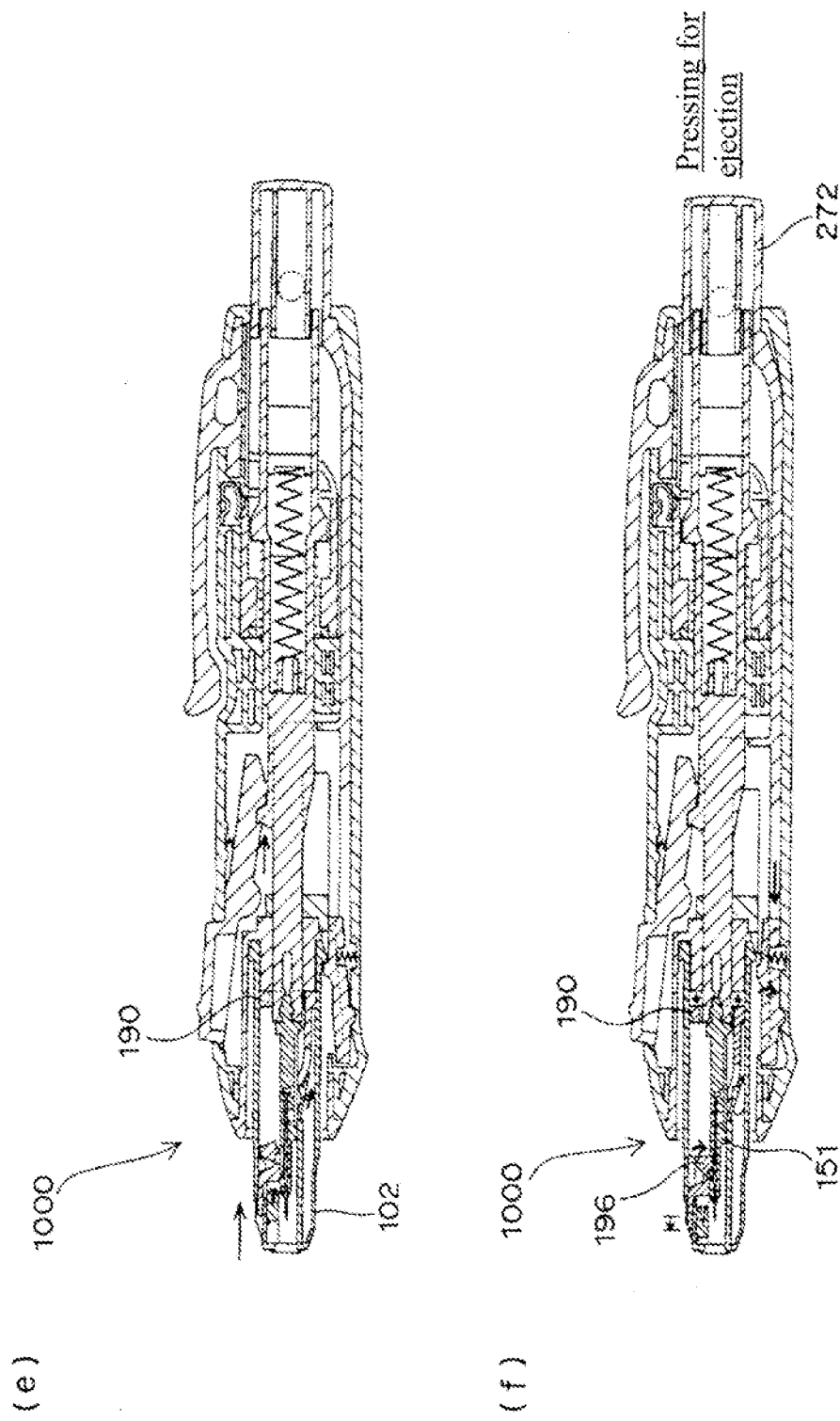

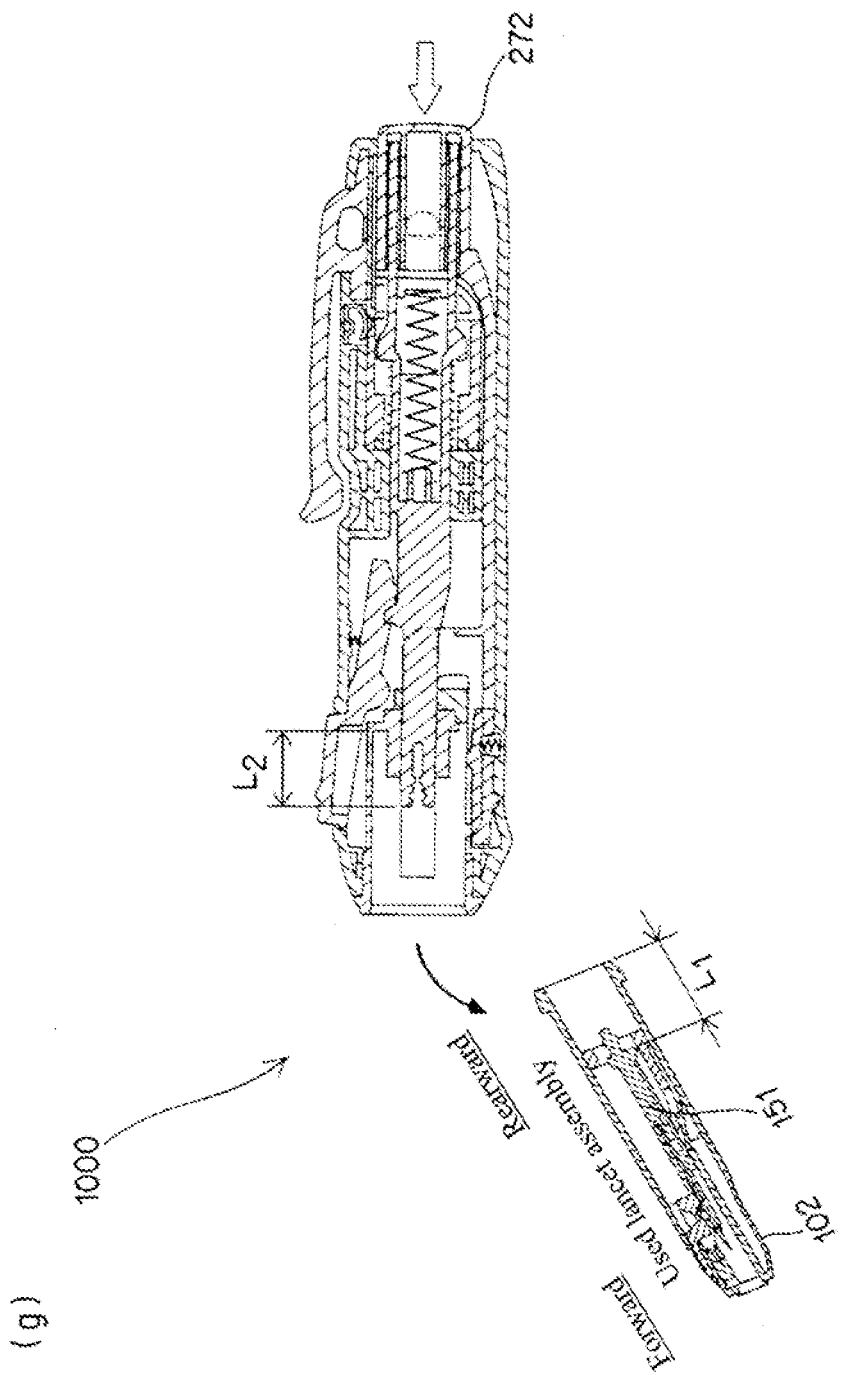

Fig. 13
(a)
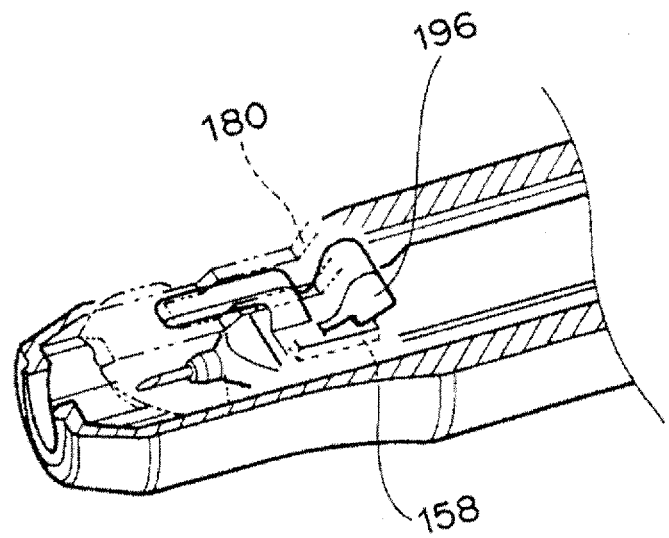
(b)
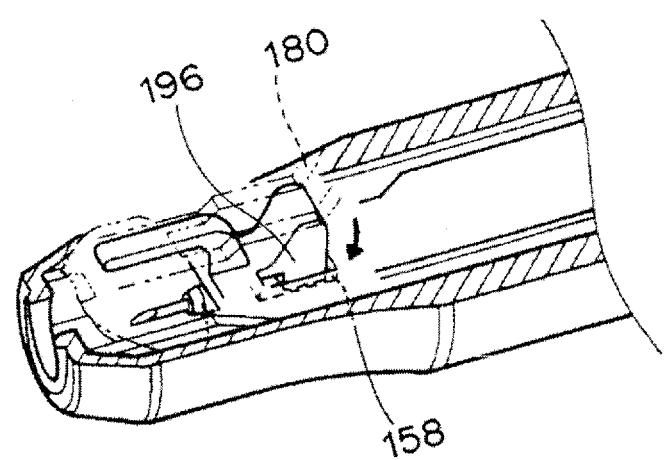

Fig. 14A
(a)
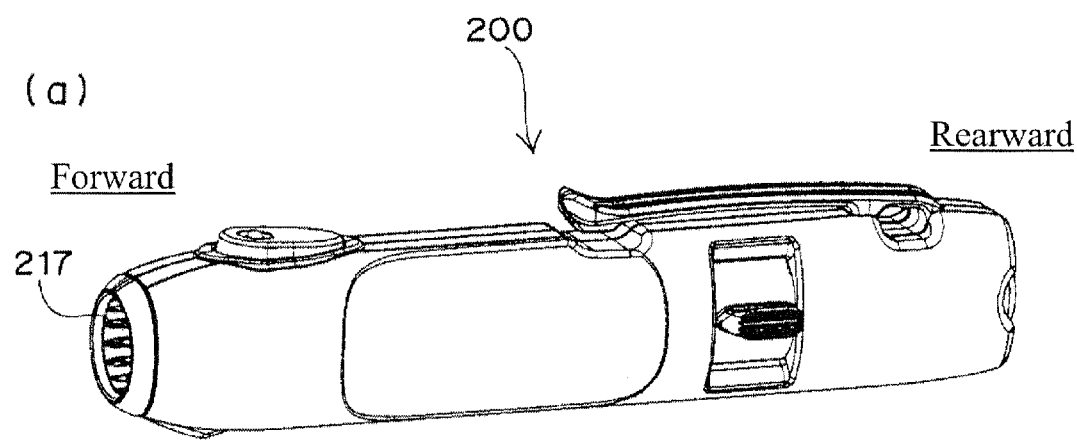
(b)
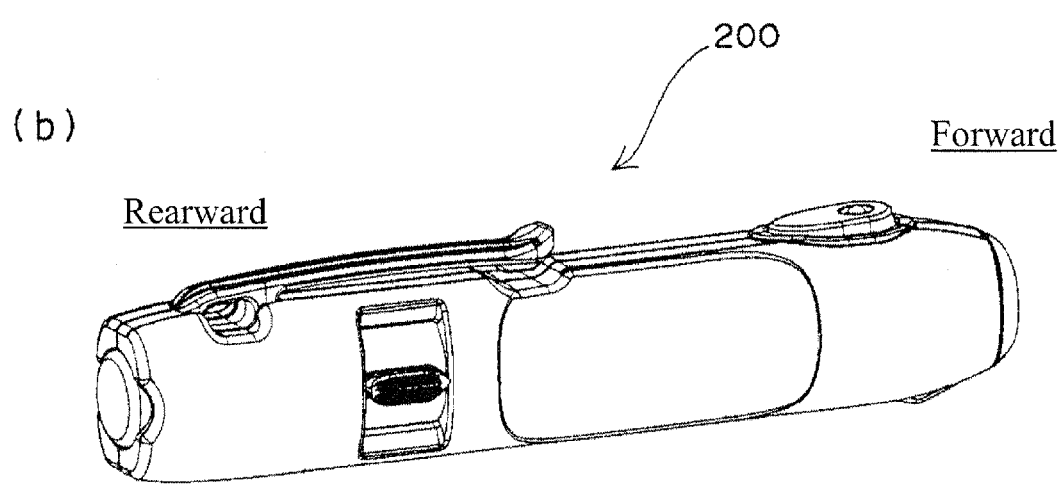

Fig. 15
(a)
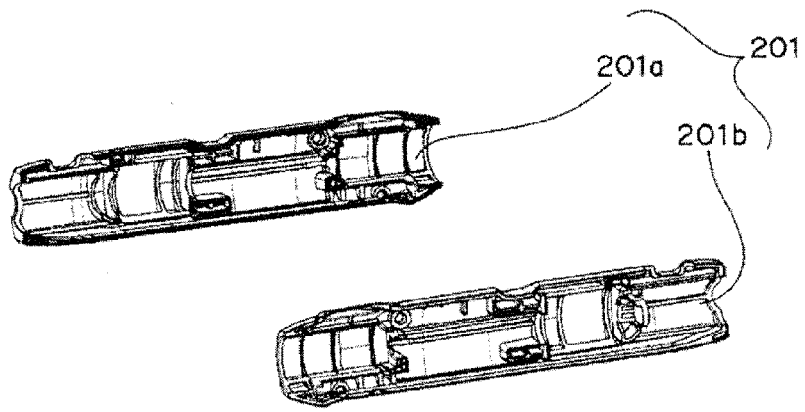
(b)
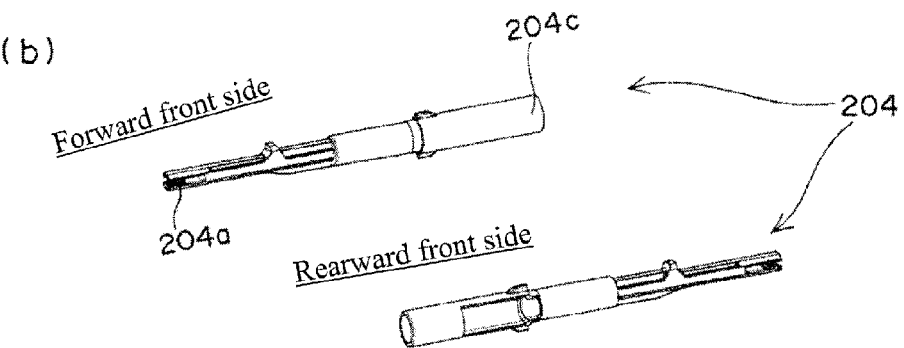
(c)
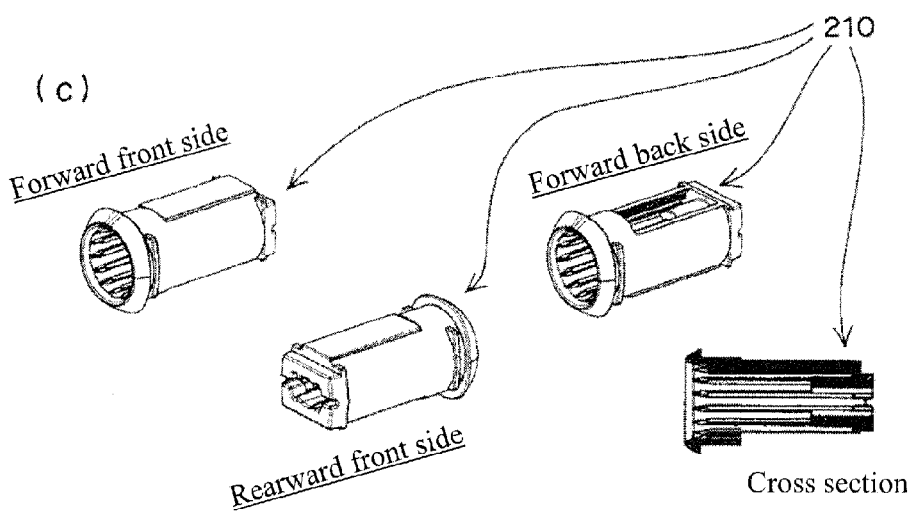
Cross section

Fig. 16
(a)
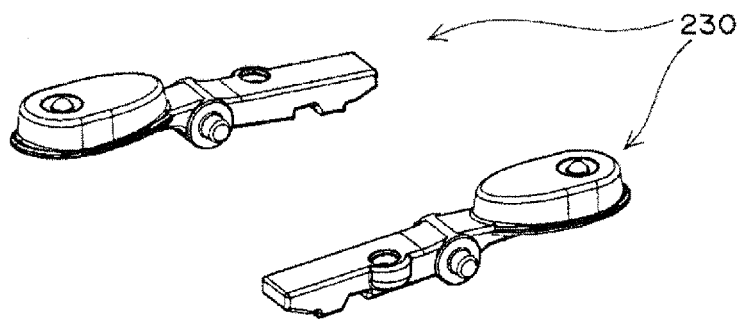
(b)
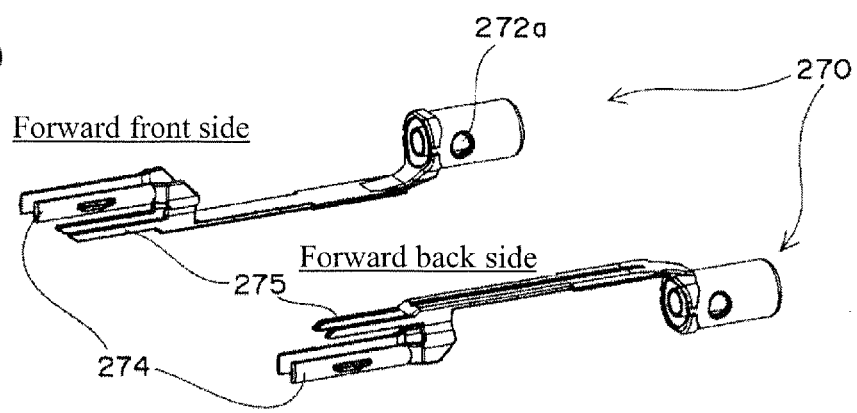
(c)
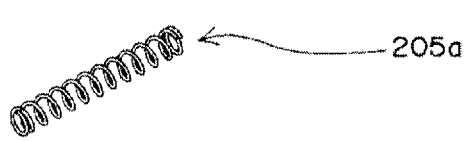
(d)
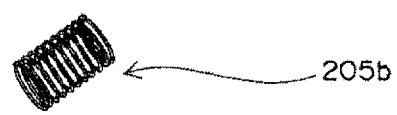

Fig. 17
(a)
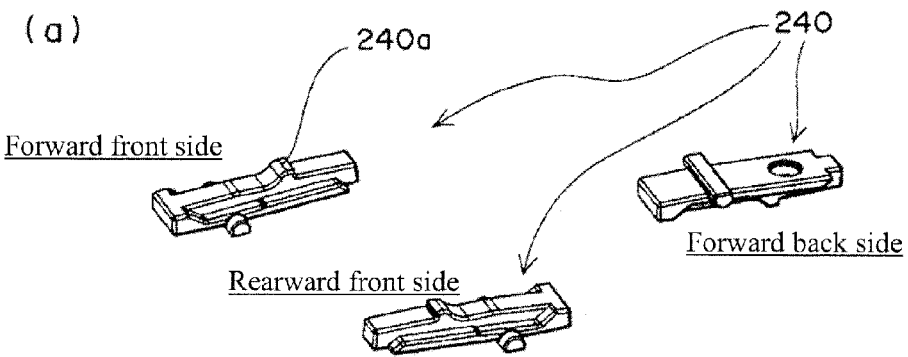
(b)
(c)
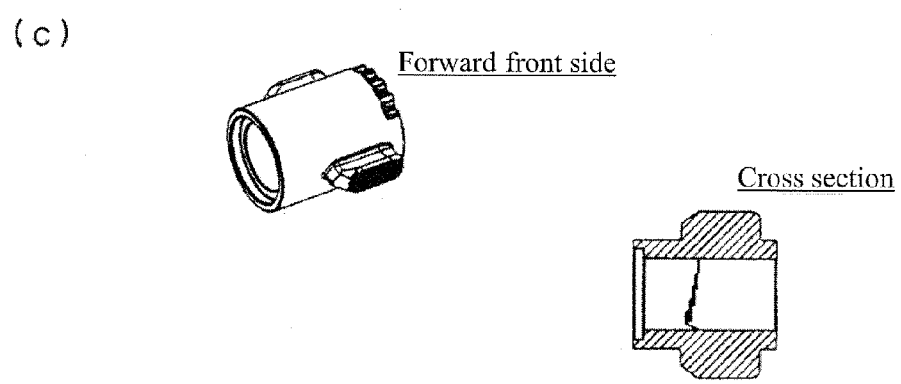
(d)

LANCET ASSEMBLY AND PRICKING DEVICE

TECHNICAL FIELD

The present invention relates to a lancet assembly which serves to prick, and also relates to an injector used in combination with the lancet assembly. Furthermore, the present invention relates to a pricking device composed of the lancet assembly and the injector. The pricking device is used for pricking a predetermined region of a human body with a sharp pricking component (e.g. a needle) so as to take a sample of body fluids (e.g. blood).

BACKGROUND OF THE INVENTION

In order to measure a blood sugar level of the patient with diabetes, it is required to take a sample of the blood from the patient. The pricking device is generally composed of a lancet and an injector wherein the lancet has a pricking component capable of puncturing a predetermined region of the patient's body. The injector has a function of launching the lancet toward a predetermined region. The pricking device can be set up for use by loading (or charging) the lancet into the injector. Due to an expansion of the compressed spring of the injector, the lancet is launched toward the predetermined region, and thereby the predetermined region is pricked.

Pricking operation by using the pricking device requires the following nine steps from the loading of the lancet into the injector until the taking out the used lancet from the injector:

(1) Removing an injector cap from the injector;
(2) Setting the lancet into the injector;
(3) Removing a lancet cap from the lancet so as to expose the tip of the pricking component;
(4) Putting the injector cap (which has been removed in step (1)) onto the injector;
(5) Cocking the injector to put the lancet in the loaded state (i.e., make the lancet ready to be launched);
(6) Applying the front end opening of the injector onto a region to be pricked, and then pressing a trigger button to launch the lancet;
(7) Removing the injector cap from the injector;
(8) Putting a protective cap on the exposed tip of the pricking component so as to shield the tip of the pricking component from its surroundings; and
(9) Ejecting the lancet from the injector, and then disposing of the used lancet.

Carrying out the above nine steps sequentially is cumbersome and thus it is desired to reduce the number of the steps.

When taking a sample of the blood by using a pricking device, a particular attention must be paid to the handling of the used lancet. In the used lancet, the tip of the pricking component is exposed on the front end of a lancet body, and there may be the patient's blood adhered to the pricking component (particularly the tip of the pricking component) due to the pricking. If the body of a person other than the subject of the blood sampling (for example, a nurse or medical practitioner who collects the blood sample) accidentally should touch the tip of the pricking component, the body of such person may be pricked by the pricking component. This will result in a wound of the body through which the patient's blood may enter the body (i.e., the body of the nurse or medical practitioner), and thus posing a risk of the infection disease.

The presently-used pricking devices are not necessarily designed with due consideration with respect to the handling of the used lancet. It has been proposed to cover the exposed tip of the pricking component with a protective cap after the pricking component is used (see U.S. Pat. No. 5,385,571). However, the covering the tip of the pricking component with the protective cap in itself will carry risk. That is, the lancet with the exposed tip of the pricking component has to be handled when the protective cap is placed thereon. Therefore the risk as described above is still not avoided.

As can be seen from the above, the pricking device requires utmost attention in handling the used lancet. Therefore, there is a demand for a pricking device in that it is allowed to be disposed of in safety after use (i.e., after the pricking operation).

SUMMARY OF THE INVENTION

The present invention has been devised to address the problems described above. Therefore, an object of the present invention is to provide a pricking device capable of collecting a blood sample with a reduced number of steps by using a lancet, and disposing of the used lancet more safely after pricking.

In order to achieve the above object, the present invention provides a lancet assembly comprising:
a lancet;
a lancet engaging part; and
a lancet case housing the lancet and the lancet engaging part, wherein the lancet comprises a lancet body, a lancet cap and a pricking component, the lancet body and the lancet cap being made of resin and the pricking component being made of metal, the pricking component is disposed in both the lancet body and the lancet cap, the tip of the pricking component is covered with the lancet cap, and the lancet cap and the lancet body are integrally connected together by a bridging component;

the lancet engaging part and the lancet cap are disposed such that the lancet engaging part and the lancet cap are capable of making contact with each other;

when the lancet engaging part is forced to be moved forward with respect to the lancet or lancet case in a pricking direction, the lancet cap is pressed by the lancet engaging part, and thereby the bridging component is broken so that the lancet cap is separated from the lancet body to expose the tip of the pricking component while the pricking component remains disposed in the lancet body; and when the lancet engaging part is forced to be further moved forward, the separated lancet cap moves to the position off a pricking pathway of the pricking component within the lancet case.

One of the characterizing features of the lancet assembly according to the present invention is that the lancet assembly comprises three parts, i.e., the "lancet", the "lancet engaging part" and the "lancet case". Another characterizing feature of the lancet assembly according to the present invention is that the lancet engaging part of the lancet assembly at least serves to "remove the lancet cap" and "prevent a re-use of the lancet", which will be described.

In a preferred embodiment of the lancet assembly according to the present invention, the lancet cap is capable of making contact with a forward-projecting portion provided within an injector (i.e., a device for launching the pricking component). When the lancet case is inserted through a front end opening of the injector to load the lancet assembly into the injector, a rear end portion of the lancet engaging part comes into contact with the forward projecting portion of the injector. When the lancet case is forced to be further inserted, there is generated a forward force for moving the lancet engaging part forward with respect to the lancet case because of the contact of the lancet engaging part with the forward projecting portion of the injector. Accordingly, the lancet cap is pressed by the lancet engaging part to be separated from the lancet body. In other words, the lancet cap is pressed forward by the lancet engaging part under such a condition that the lancet body is secured within the lancet case, and thereby a force for moving the lancet cap and the lancet body away from each other is generated. This results in the breaking of the bridging component which interconnects the lancet cap and the lancet body. More specifically, the lancet body is temporarily secured to the lancet case, and thereby the lancet body can move together with the inserted lancet case in the direction of the insertion. On the other hand, the lancet cap is not secured to the lancet case. Therefore, when the lancet cap is pressed by the lancet engaging part which is in an engagement with the lancet cap, the lancet body and the lancet cap are subjected to forces for moving them away from each other. When the forces eventually exceed a predetermined threshold, the bridging component which interconnects the lancet cap and the lancet body is broken. The breaking of the bridging component causes the lancet cap to be separated from the lancet body, and thereby the tip of the pricking component is exposed. When the lancet case is further inserted into the injector after the breaking of the pricking component, the separated lancet cap is pushed by the lancet engaging part, and thereby the separated lancet cap moves within the lancet case and finally reaches the position that is off the pricking pathway.

As can be appreciated from the above, the lancet assembly of the present invention is characterized in that the loading (i.e., charging of the lancet assembly into the injector) makes it possible not only for the lancet cap to be separated from the lancet body, but also for the separated lancet cap to move to the position that is off the pricking pathway. The term "forward" used herein substantially means the pricking direction, i.e., the direction in which the pricking component is launched (or the direction in which the lancet body with the tip of the pricking component exposed is launched). The term "rearward" used herein substantially means the direction opposite to the forward direction. The "forward" has substantially the same meaning as the "pricking direction" and also the "pricking direction" corresponds to the "pricking pathway direction". Furthermore, the phrase "off a pricking pathway of the pricking component" used herein substantially implies that the separated lancet cap does not impede a forward launch of the lancet body (more specifically, the lancet body having the exposed tip of the pricking component) and also does not impede the pricking of the pricking component moving in the pricking direction. Since the launch and the prick are not impeded by the separated lancet cap, the pricking component can suitably puncture the predetermined region. Preferably, the phrase "off the pricking pathway of the pricking component" implies that the launched lancet body does not touch the separated lancet cap at all.

In a preferred embodiment, the lancet engaging part has a hollow configuration. More specifically, the lancet engaging part is configured to have a hollow portion around a central axis thereof, the central axis extending along the pricking direction. The lancet engaging part and the lancet are preferably in an assembled state with each other such that the lancet is located in the hollow portion of the lancet engaging part.

It is preferred that the lancet engaging part comprises a pair of cap pressing portions which are capable of making contact with a rear end portion of the lancet cap. The phrase "capable of making contact" used herein means such a state that the cap pressing portion of the lancet engaging part and the rear end portion of the lancet cap are positioned adjacent to each other. Thus, the phrase "capable of making contact" means that the cap pressing portion of the lancet engaging part and the rear end portion of the lancet cap are already in contact with each other or they can be brought into contact with each other only by causing the cap pressing portion to be slightly moved.

Since the lancet cap can be separated from the lancet body in the lancet assembly according to the present invention, the tip of the pricking component is exposed while the pricking component remains situated in the lancet body. When the lancet case is inserted further into the injector after the separation of the cap, the separated lancet cap is pressed by the lancet engaging part. Therefore, the lancet body and the lancet cap are subjected to the forces for moving them away from each other, which causes the separated lancet cap to move within the lancet case and deviate from the pricking pathway. In order to guide the separated lancet cap to the position off the pricking pathway, it is preferred that the lancet case is equipped with a slope component. In this regard, it is preferred that the lancet cap is optionally provided with a sloped portion having a shape corresponding to the slope component of the lancet case.

The lancet body is temporarily secured in the lancet case. Preferably, the lancet body is secured such that the lancet body is prevented from being moved forward. For example, it is preferred at a point in time before the lancet cap is separated that the forward movement of the lancet body is inhibited by a mutual engagement between an engagement portion "A" provided within the lancet case and an engaged portion "B" of the lancet body. In other words, a part of the lancet body abuts against an internal structure of the lancet case such that they engage with each other, and thereby the forward movement of the lancet body is inhibited. In this case, the mutual engagement between the engagement portion "A" and the engaged portion "B" is finally released after the lancet cap is separated. This means that the secured state of the lancet body within the lancet case is finally released. In this regard, the lancet engaging part comprises, for example, a disengagement portion for releasing the mutual engagement between the engagement portion "A" of the lancet case and the engaged portion "B" of the lancet body. It is preferred at a point in time after the lancet cap is separated from the lancet body that the disengagement portion of the lancet engaging part, when being forced to be moved forward, presses the engagement portion "A" to outwardly displace the engagement portion "A", and thereby the mutual engagement between the engagement portion "A" and the engaged portion "B" is released. The releasing of the mutual engagement allows the lancet body with the tip of the pricking component exposed to be launched in the pricking direction for the pricking.

In a preferred embodiment of the lancet assembly according to the present invention, the lancet and the lancet engaging part are accommodated within the lancet case without being exposed from the lancet case. More specifically, the lancet and the lancet engaging part are accommodated as a whole within the lancet case such that both of the lancet and the lancet engaging part do not project from the lancet case.

In a preferred embodiment, a partial cutout is provided in a body of the lancet case, and the lancet engaging part is provided with an indicator portion. It is preferred in this case that, when the lancet engaging part is forced to be moved forward to such a position that the separated lancet cap is positioned off the pricking pathway, the indicator portion of the lancet engaging part becomes exposed from the partial cutout of the lancet case. This makes it possible to visually recognize from the outside whether or not the lancet cap has been already separated from the lancet body, i.e., whether or not the lancet assembly can be ready for pricking.

In another preferred embodiment, the rear end portion of the lancet body has an engaging portion capable of engaging with the plunger of the injector. For example, the engaging portion of the rear end portion of the lancet body fits into a recessed portion provided in the front end of the plunger wherein the recessed portion of the plunger is formed by partially splitting the front end of the plunger. In this case, the pushing of the engaging portion of the lancet body can expand the front end of the plunger so that the engaging portion of the lancet body enters the front end of the plunger, and thereby the engaging portion slots into the front end. In another embodiment, the engaging portion of the rear end portion of the lancet body may fit into the front end of the plunger in a press fitting relationship. Due to such relationship, the rear end portion of the lancet body and the front end of the plunger of the injector can engage with each other when the lancet assembly is loaded in the injector by inserting the lancet case through the front end opening of the injector. Accordingly, when the lancet body is secured to the lancet case, the inserting of the lancet case into the injector enables the lancet body to push the plunger rearward (that is, the plunger can be retracted). When the plunger is pushed rearward, the force required for launching the pricking component is stored in plunger. It is preferred that the disengagement between the engagement portion "A" of the lancet case and the engaged portion "B" of the lancet body is done at a point in time after the rear end portion of the lancet body makes engagement with the plunger of the injector.

The present invention also provides an injector for launching the lancet body with the tip of the pricking component being exposed, the injector being used in combination with the above described lancet assembly. The injector comprises:

a plunger which is capable of engaging with a rear end portion of a lancet body and causing a launch of the lancet body in a pricking direction;

a lancet assembly receiving part which is provided at a front end opening of the injector and includes therein the forward-projecting portion, the lancet assembly receiving part being in a cylindrical form; and a trigger lever for triggering the launch of the pricking component when the trigger lever is pressed from the outside for the purpose of pricking. The injector has such a configuration that the lancet assembly can be loaded into the injector so that a part of the lancet case is accommodated in the lancet assembly receiving part of the injector. When the lancet assembly with a forward movement of the lancet body being inhibited is loaded into the injector, the lancet engaging part abuts against the forward-projecting portion of the lancet assembly receiving part. When the lancet case is forced to be further inserted, a forward force for moving the lancet engaging part forward with respect to the lancet case is applied to the lancet engaging part due to the abutment of the lancet engaging part with the forward projecting portion of the lancet assembly receiving part. This makes it possible to separate the lancet cap from the lancet body, and thereby the separated lancet cap can be forced to be moved to the position off the pricking pathway.

In a preferred embodiment according to the present invention, the injector further comprises a case locking part on a front sided-inner wall of a housing of the injector. A surface of the case locking part is equipped with a stopper which projects toward the inside of the injector. A spring is provided between the case locking part and a sidewall of a housing of the injector so that an inward force toward the inside of the injector is applied to the case locking part. Accordingly, when the lancet assembly is loaded into the injector, a locking projection provided on an outer wall surface of the lancet case slides on the case locking part, and after the sliding locking projection rides over the stopper, the locking projection and the stopper become capable of engaging with each other so that the loaded lancet case cannot come off the injector.

The injector according to the present invention further may comprise an ejector. The ejector serves to eject the loaded lancet assembly from the injector. In this case, when the ejector is forced to be moved after the pricking, the ejector abuts against the rear end portion of the lancet engaging part, and thereby a pressing action is applied to the lancet engaging part. Thus, when the ejector is forced to be moved forward, the lancet engaging part is caused to be moved forward within the lancet case. The lancet engaging part, when being forced to be moved forward, makes engagement with an inner wall of the lancet case at its front end. This means that the front end of the lancet engaging part pushes against the inner wall of the lancet case. Accordingly, when the ejector is forced to be further move forward, a force for pushing the whole of the lancet assembly forward is occurred so that the lancet assembly is finally ejected from the injector. The ejector may have an unlocking portion. The unlocking portion is in such an elongate form that it projects forward. In this case, when the ejector is forced to be moved forward after the pricking, the unlocking portion of the ejector abuts against the case locking part, and thereby forcing the case locking part to move outwardly. This causes a releasing of the engagement between the locking projection and the stopper. It is preferred that a flexible locking portion of the lancet engaging part suitably functions upon the driving operation of the ejector. Specifically, when the lancet engaging part is pushed by the ejector to be moved forward with respect to the lancet case at a point in time after the launch of the pricking component, the flexible locking portion of the lancet engaging part abuts against an inner-wall raised portion of the lancet case to displace the flexible locking portion inwardly, and thereby at least one part of the flexible locking portion is finally located in the recess portion of the lancet body. It is also preferred that an indicator of the injector suitably functions upon the moving of the ejection at a point in time after the pricking operation. Specifically, when the lancet engaging part is pushed by the ejector to be moved forward within the lancet case, an indicator portion of the lancet engaging part is furthermore exposed from a partial cutout of the lancet case. This makes it possible to visually recognize from the outside whether or not the lancet assembly has been already used.

It is particularly preferred that the ejector of the injector has an elongate shape as a whole. In this case, it is also preferred that a rear end portion of the elongate ejector is equipped with a force point to be used for a forward movement of the ejector. It is preferred that the ejector is disposed such that the force point of the ejector is exposed from a housing of the injector. Furthermore, it is preferred that a partial cutout is provided at a position of the force point of the ejector. When a sufficient force required for launching the pricking device is stored due to the retraction of the plunger, a rear end portion of the plunger is preferably exposed from the partial cutout from the ejector.

In the used lancet assembly after being ejected from the injector, the lancet body can be located at the most forward position within the lancet case, compared with that before being used. As a result, even if the used lancet assembly is loaded into the injector, the rear end portion of the lancet body and the plunger of the injector no longer have a positional relationship which allows them to engage with each other. In other words, even if the used lancet assembly is loaded into the injector, the plunger cannot be retracted, and thus the used lancet assembly cannot become ready for pricking any more.

The present invention also provide the lancet and the lancet case of the above described lancet assembly. Furthermore, the present invention provides a pricking device composed of the lancet assembly and the injector. Still furthermore, the present invention provides a pricking device kit in which the lancet assembly of the present invention and the injector of the present invention are provided to form the pricking device.

Effect of the Invention

The lancet assembly of the present invention can be combined with the injector of the present invention so as to provide the pricking device. In this regard, the pricking device can be made ready for pricking only by inserting the lancet case into the injector. Thus, it is made possible to launch (or cock) the lancet without the need of a removal of the lancet cap by hand (or by fingers). Furthermore, the pricking device of the present invention makes it possible to discharge the used lancet case (in which the used pricking component is contained) more safely from the injector, simply by operating the ejector (namely just by sliding the ejector) after pricking. As a result, the pricking operation can be completed through substantially only three steps as follows: (i) step of loading the lancet assembly into the injector; (ii) step of pricking; and (iii) step of discharging of the lancet assembly by using the ejector.

In the lancet assembly of the present invention, the lancet is accommodated in the lancet case without being exposed from the lancet case at any point in time both before being used and after being used. In other words, the lancet is in a more hygienic state since the lancet is isolated to some extent from its surrounding environment. Especially at a point in time after pricking, the locking portion of the lancet engaging part can function to limit the movement of the lancet body, so that the used lancet (i.e., pricking component) would not come off the case. As such, the lancet device according to the present invention is a safety device.

Furthermore, the lancet assembly of the present invention has an indicator function, making use of the lancet engaging part. In this regard, the user can visually and readily recognize whether or not the lancet assembly is now ready for pricking, as well as whether or not the lancet assembly has been already used. As such, the lancet device according to the present invention is a more convenient lancet device.

BRIEF DESCRIPTION OF THE DRAWINGS

FIGS. 1(a) and 1(b) are perspective views of a lancet assembly, respectively.

FIGS. 6(a) through 6(c) are perspective views illustrating an appearance of a lancet, respectively.

FIG. 8A includes vertical and horizontal cross sectional views illustrating an internal structure of the lancet assembly (in a state before the lancet assembly is used).

FIG. 8B includes vertical and horizontal cross sectional views illustrating the internal structure of the lancet assembly (in a state after the lancet cap is separated).

FIG. 8C includes vertical and horizontal cross sectional views illustrating the internal structure of the lancet assembly (in a state after the lancet assembly is used).

FIGS. 9A(a) and 9A(b) are cross sectional views respectively illustrating the lancet assembly and an injector in its use.

FIGS. 9B(c) and 9B(d) are cross sectional views respectively illustrating the lancet assembly and an injector during their use.

FIGS. 9C(e) and 9C(f) are cross sectional views respectively illustrating the lancet assembly and an injector during their use.

FIG. 9D(g) is cross sectional view illustrating the lancet assembly and an injector during their use.

FIGS. 13(a) and 13(b) are schematic perspective views illustrating a displacement of a flexible locking portion.

FIGS. 14A(a) and 14A(b) are perspective views of the injector.

FIGS. 15(a) through 15(c) are perspective views respectively illustrating various components of the injector (i.e., FIG. 15(a): housing, FIG. 15(b): plunger, and FIG. 15(c): lancet assembly receiving part).

FIGS. 16(a) through 16(d) are perspective views respectively illustrating various components of the injector (i.e., FIG. 16(a): trigger lever, FIG. 16(b): ejector, FIG. 16(c): fire spring, and FIG. 16(d): return spring).

FIGS. 17(a) through 17(d) are perspective views respectively illustrating various components of the injector (i.e., FIG. 17(a): case locking part, FIG. 17(b): hook, FIG. 17(c): adjuster, and FIG. 17(d): adjuster ring).

BEST MODES FOR CARRYING OUT THE INVENTION

Figure 2:
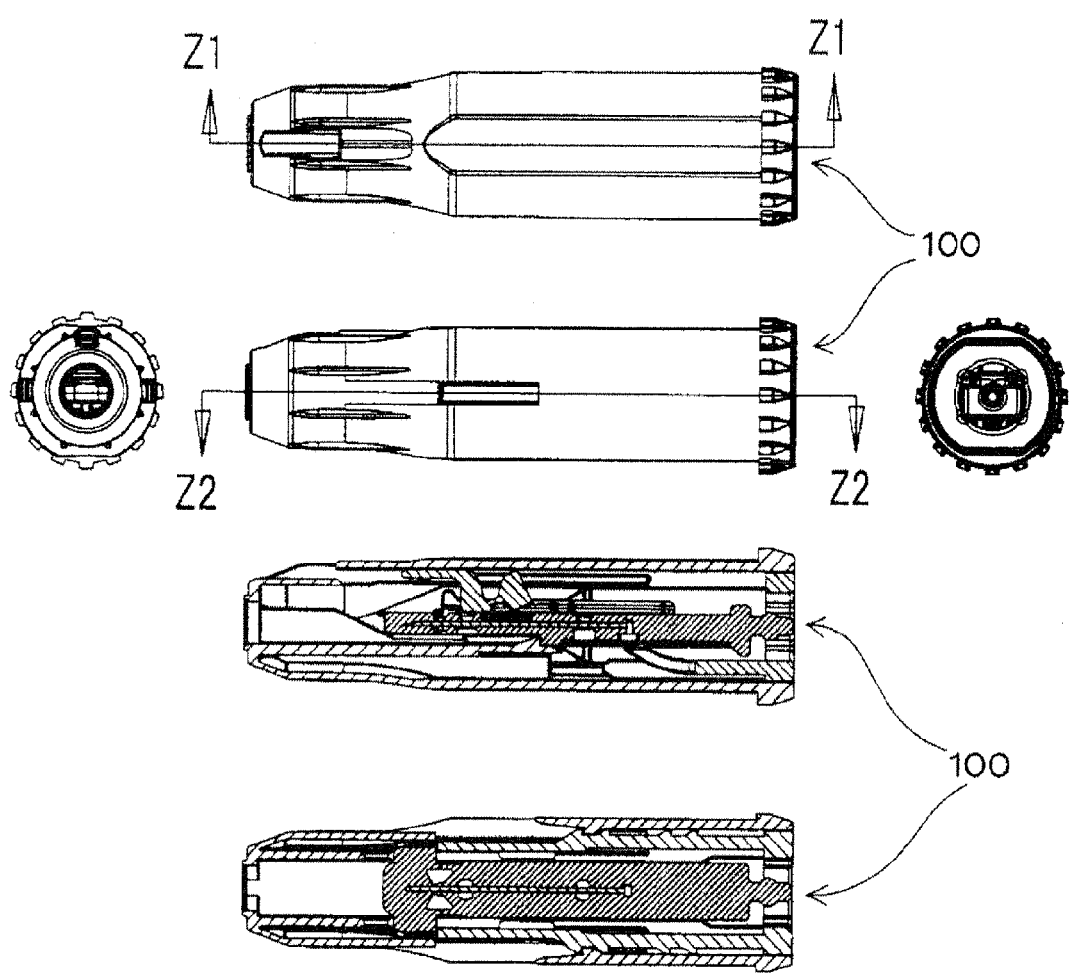
FIG. 2 includes appearance views and cross sectional views of the lancet assembly.

With reference to the accompanying drawings, a lancet assembly of the present invention as well as a lancet and a lancet case that constitute the lancet assembly will be described in detail. An injector to be used in combination with the lancet assembly will also be described in detail. The explanation about a pricking device composed of the lancet assembly and the injector is included in the descriptions of the lancet assembly and the injector.

Throughout the claims, the description and the abstract, the word "forward" means the pricking direction in which the lancet moves for pricking (namely, the direction in which the pricking component moves for pricking), and the word "rearward" means the direction opposite to the forward. These directions are indicated in the drawings. It should be noted that "pricking direction" corresponds to a direction from an opening end of the lancet case toward a pricking opening of the lancet case, such direction being the same as the "forward".

<Basic Structure of Lancet Assembly>

Figure 3:
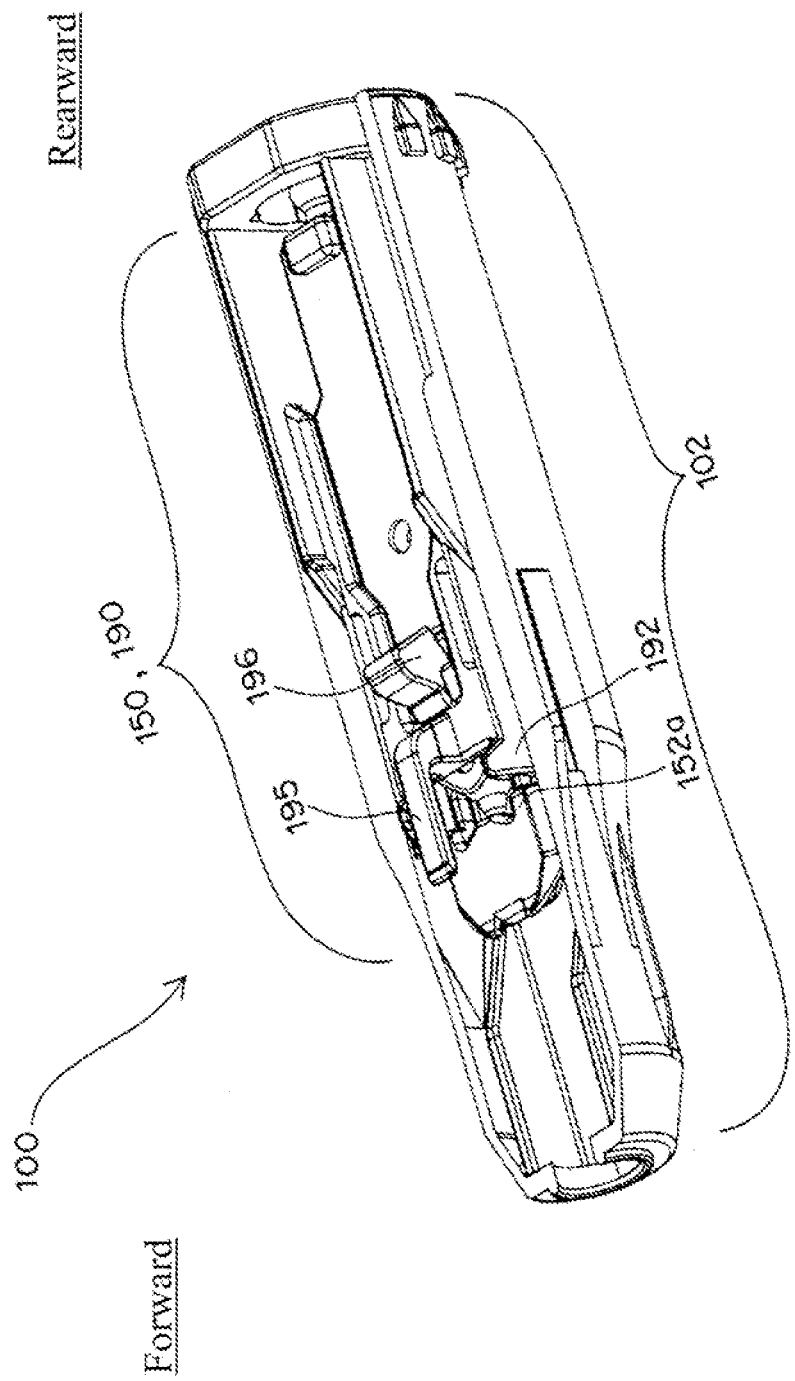
FIG. 3 is a perspective view illustrating an internal structure of the lancet assembly.
Figure 4:
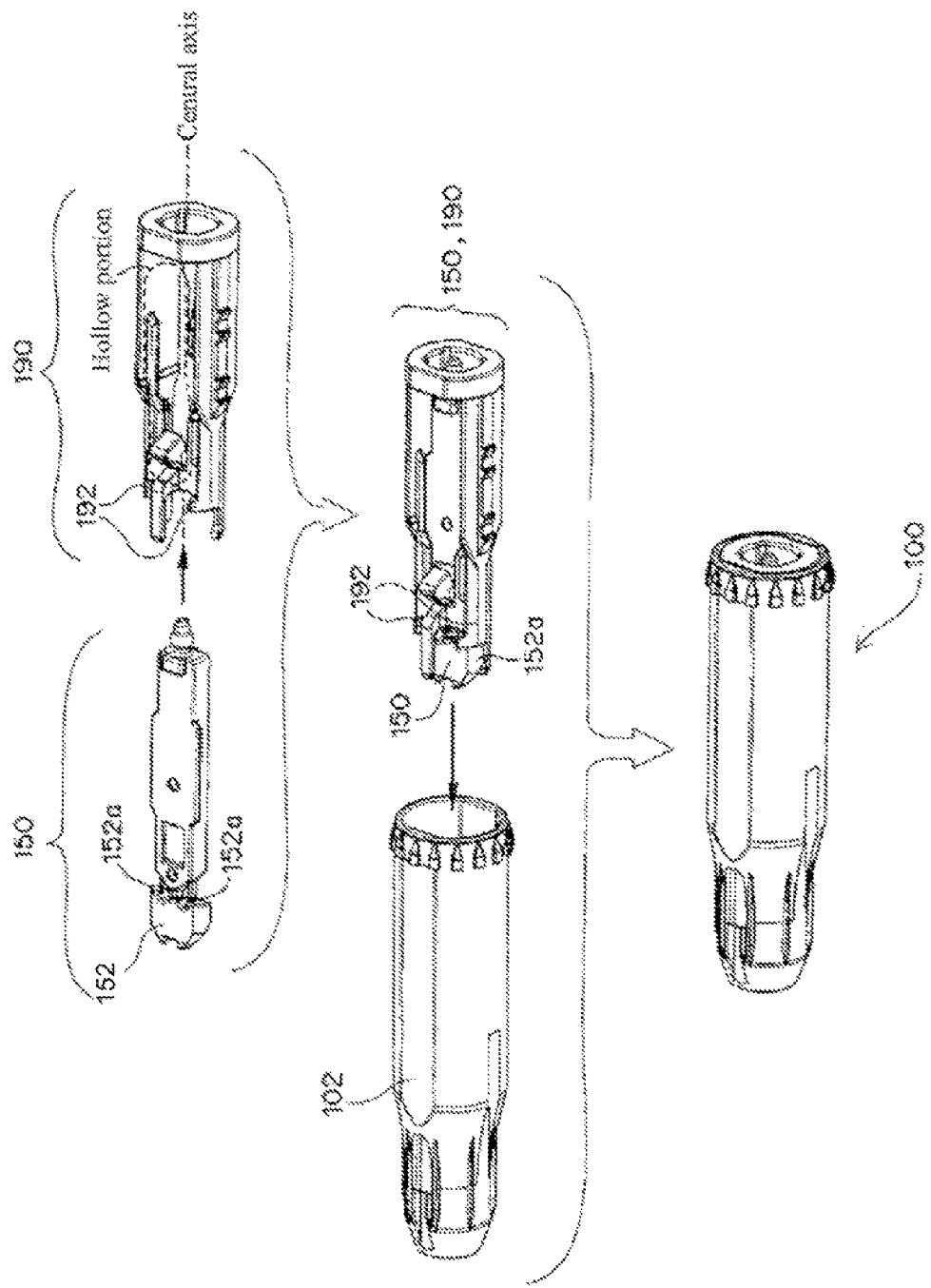
FIG. 4 includes exploded perspective views of the lancet assembly.

FIGS. 1 to 4 illustrate a lancet assembly 100. FIG. 1 includes appearance views of the lancet assembly 100. FIG. 2 includes side views of the lancet assembly 100 and the corresponding cross sectional views thereof. FIG. 3 illustrates the lancet assembly 100 with a half of a lancet case cut away along a longitudinal direction of the lancet assembly 100 for the sake of easy understanding of an internal structure of the lancet assembly 100. FIG. 4 includes exploded views and development views of the lancet assembly 100 for the sake of easy understanding of constituent parts of the lancet assembly 100.

As illustrated in FIGS. 3 and 4, the lancet assembly 100 has such a configuration that a lancet 150 and a lancet engaging part 190 are accommodated within a lancet case 102. Namely, the lancet assembly 100 of the present invention substantially comprises three parts, i.e., the "lancet 150", the "lancet engaging part 190" and the "lancet case 102".

More specifically, as illustrated in FIGS. 3 and 4, the lancet 150 and the lancet engaging part 190 are in an assembled state such that the lancet 150 is located in a hollow portion of the lancet engaging part 190, the hollow portion being positioned in an inside region of the lancet engaging part. The assembled lancet and lancet engaging part is accommodated within the lancet case 102. In other words, the lancet engaging part 190 is positioned around the lancet 150, and the lancet case 102 is provided so as to surround the assembly of the lancet 150 and the lancet engaging part 190 as a whole. In particular, the lancet 150 and the lancet engaging part 190 are disposed with each other such that a pair of case pressing portions 192 of the lancet engaging part can make contact with rear end portions 152a of a lancet cap 152 (see FIG. 4).

In the following, components or parts regarding the lancet assembly 100 will be described.

(Lancet Case)

Figure 5:
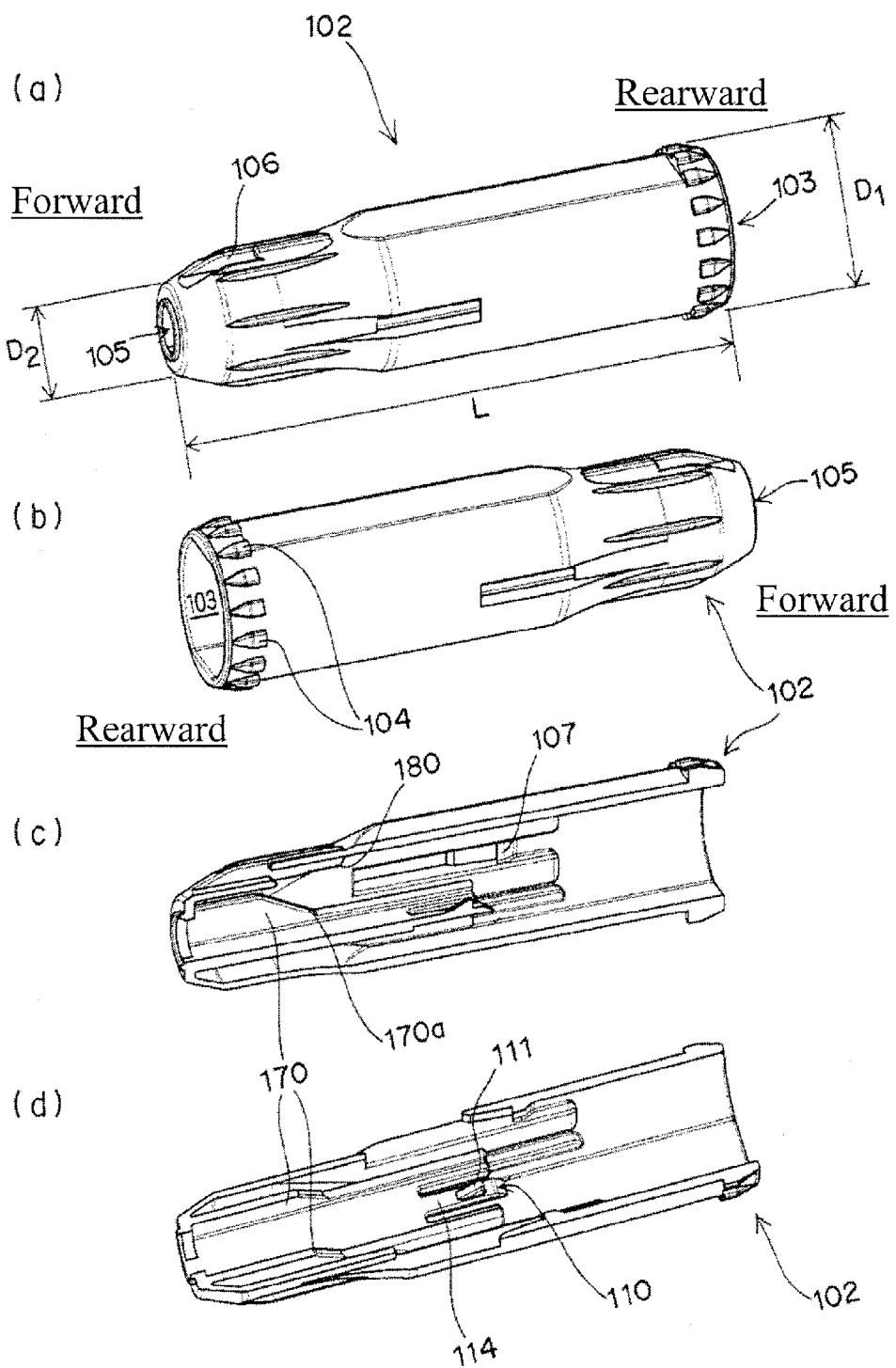
FIGS. 5(a) through 5(d) are perspective views illustrating an appearance and an internal structure of a lancet case, respectively.

As illustrated in FIG. 5, the lancet case 102 has, for example, a cylindrical shape as a whole. Such case 102 has relatively small dimensions. In this regard, the lancet case 102 may have the following dimensions (L, $D_1$, $D_2$) as shown in FIG. 5. For instance, a length L can be in the range of 28 to 52 mm (for example, about 40 mm), a diameter $D_1$ can be in the range of 0.7 to 1.3 mm (for example, about 10 mm) and a diameter $D_2$ can be in the range of 3.5 to 6.5 mm (about 5 mm). The shape of the case 102 is not necessarily limited to the cylindrical shape, and thus may be, for example rectangular tube shape.

The lancet case 102 may be formed of any kind of resin material which is used for lancets in general. The lancet case 102 has a rear opening end 103 and a pricking opening 105 which is opposed to the rear opening end. The pricking opening 105 is a portion applied to the region (e.g., finger) to be pricked.

As illustrated in FIG. 5(b), projections 104 are provided on an outer surface of the lancet case (specifically, the projections 104 are provided on the outer surface of the case at a rear end region). Preferably, a plurality of projections 104 which are provided on a body of the lancet case are arranged annularly in a circumferential direction of the body of the lancet case. The plurality of projections 104 serve to cooperate with a plurality of guiding projections of an injector (see, guiding projections indicated by reference numeral 217 in FIGS. 14A and 14C) upon an insertion of the lancet case into the injector. This allows the lancet case to be smoothly inserted into the injector. The projections 104 themselves can also serve as "locking projections" for allowing the lancet case which has been once inserted into the injector to be kept retained in the injector. Specifically, after the loading of the lancet assembly into the injector is completed, the projection 104 of the lancet case become capable of engaging with a case locking part (see, the part indicated by reference numeral 240 in FIG. 14C) of the injector. More specifically, the projection 104 of the inserted lancet case can engage with a stopper 240a of the case locking part after the loading of the lancet assembly into the injector is completed.

As illustrated in FIG. 5(a), it is preferred that a partial cutout 106 is provided at an outer surface region of the lancet case. Specifically, the partial cutout 106 is preferably provided at a front side region of the case. The partial cutout 106 can serve as an indicator. Because of the existence of the partial cutout 106, an indicator portion (see, the portion indicated by reference numeral 195 in FIG. 3) provided within the lancet case can be exposed according to a movement of the lancet engaging part.

An engagement portion "A" (110) for preventing a body of the lancet from being moved forward is provided in an internal portion of the lancet case 102 (see FIG. 5(d) in particular). As illustrated in FIG. 5(d), the engagement portion "A" (110) has such a form that it projects toward an internal center of the injector (i.e., the engagement portion "A" is provided with a projection 111). The engagement portion "A" has an elongated section 114 with an outwardly flexible free end provided therein.

As illustrated in FIGS. 5(c) and 5(d), a slope component 170 which allows a sliding movement of the separated lancet cap is provided in the lancet case 102. Preferably, the slope component 170 has a sloped face 170a angled with respect to a pricking direction so that the lancet cap can be suitably moved forward to the position off the pricking pathway.

It is preferred that an internal structure of the lancet case has an element contributing to a mobility prevention of the used lancet or a re-use prevention of the used lancet. Specifically, it is preferred that an internal raised portion 180 is provided as illustrated in FIG. 5(c). The internal raised portion 180 can cooperate with a flexible locking portion 196 of the lancet engaging part 190 (see FIG. 3) when the lancet assembly are used. As illustrated, the internal raised portion 180 has such a form that an internal wall of the lance case partially projects toward an internal center of the case. When the flexible locking portion 196 abuts against the internal raised portion 180, the flexible locking portion 196 is forced to be inwardly displaced (see FIGS. 8B and 8C regarding the form of the internal raised portion 180 and also the displacement of the flexible locking portion 196).

Furthermore, as illustrated in FIG. 5(c), the inner wall of the lancet case 102 is provided with a pair of projections 107 which serve to retain the lancet engaging part 190 in the case.

(Lancet)

The perspective views and a cross sectional view of the lancet 150 are respectively illustrated in FIG. 6. Similarly to the lancet case 102, the lancet 150 is also small. The lancet 150 comprises a lancet body 151, a lancet cap 152 and a pricking component 153 as shown in FIG. 6. The pricking component 153 is a metal needle or a metal blade, for example. As shown in FIG. 6(c), the pricking component 153 is situated in both of the lancet body 151 and the lancet cap 152 made of resin wherein the tip 153a of the pricking component 153 is covered with the lancet cap 152. Since the pricking component 153 is situated within the lancet body 151 and the lancet cap 152, the pricking component 153 is not shown in FIG. 6(a) and FIG. 6(b). As shown in FIG. 6(a) and FIG. 6(b), the lancet cap 152 and the lancet body 151 are integrally connected via a bridging component 154. The lancet 150 can be formed of resin (such as polyethylene or polypropylene) by inserting the pricking component 153 into a die, in a so-called insert molding process. In this case, the bridging component 154 can be formed upon carrying out the insert molding process. Accordingly, the bridging component 154 can be formed of the same resin as that of the lancet cap 152 and the lancet body 151. As shown in FIG. 6(a) and FIG. 6(b), the bridging component 154 may be a rod-like component with small diameter. In this case, it is preferred that the rod-like component is provided so as to bridge between the lancet cap 152 and the lancet body 151. The bridging component 154 may have a notch (for example, a V-shaped notch) so that the bridging component 154 can be easily broken.

The lancet cap 152 extends such that it flares in a transverse direction as illustrated in FIGS. 6(a) and 6(b). A rear end side of the flared portion 155 can be pressed by the other member. Due to such form of the lancet cap, the lancet engaging part 190 is capable of making suitable contact with the rear end portions 152a of the lancet cap. Due to the contact of the lancet engaging part 190 with the rear end portions 152a, the rear end portions 152a of the lancet cap can be pressed by the lancet engaging part 190 when the lancet assembly is used.

The body 130 of the lancet is provided such that it is temporary secured to the lancet case 102, and thus the lancet body 130 has an element therefor. Specifically, the lancet body 130 has an engaged portion "B" (135) which is cooperative with the engagement portion "A" of the lancet case (see FIG. 6(b)). For example, in a case where the engagement portion "A" (110) of the lancet case has such a form that it projects toward the internal center of the injector (see FIG. 5(d)), the engaged portion "B" (135) of the lancet body preferably has a stepped shape or a concaved shape as illustrated in FIG. 6(b). Due to the cooperation between the "projecting engagement portion A (110)" and the "stepped shaped or concaved shaped-engaged portion B (135)", the forward movement of the lancet body 130 is inhibited (see FIG. 8A, for example).

A body of the pricking component 150 is fixed in the lancet body 130. Therefore, upon pricking, the lancet body 130 is launched forward together with the pricking component 150. Further, a rear end portion of the lancet body 130 comprises an engage portion 165 for engaging with a plunger of the injector (see the portion indicated by reference numeral 204 in FIG. 14C, for example). In other words, when the lancet assembly is loaded into the injector, the rear end portion 165 of the lancet body can make engagement with a front end portion 204a of the plunger 204, thereby causing the plunger to be retracted as the insertion of the lancet case is performed. A force necessary for launching the pricking component is stored in the retracted plunger. For the sake of tight engagement of the lancet body with the plunger, the rear end portion 165' of the lancet body may have a raised shape extending in the transverse direction as illustrated.

Figure 7A:
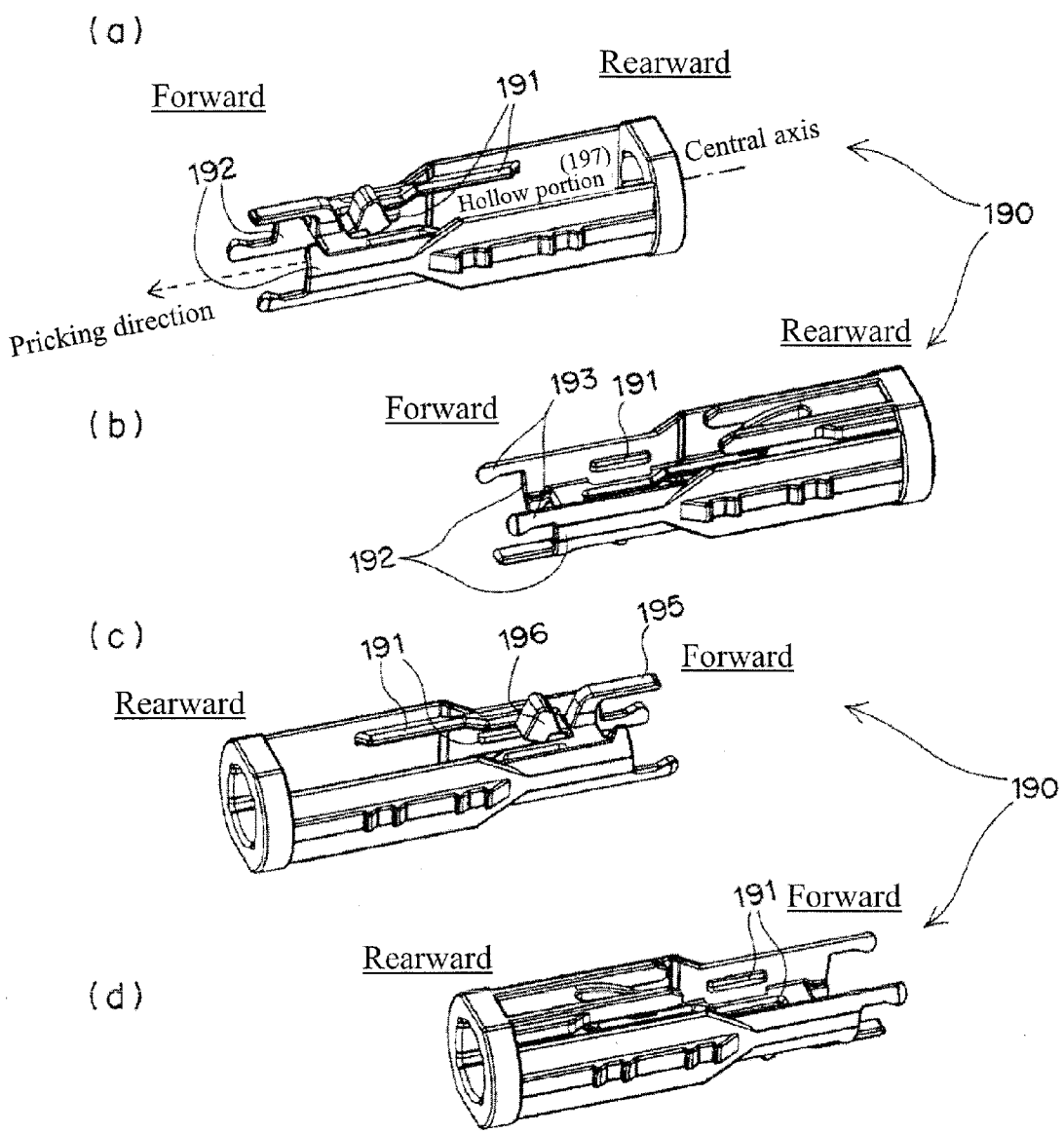
FIGS. 7A(a) through 7A(d) are perspective views illustrating an appearance of a lancet engaging part, respectively.

Whereas the lancet engaging part 190 has a guide 191, the lancet body 151 has a pair of guided component 157 configured to cooperate with the corresponding guide 191 of the lancet engaging part 190 (see FIG. 7A). As illustrated in FIGS. 6(a) and 6(b), it is preferred that the pair of guided components 157 are in a form of continuously raised sections which outwardly extend symmetrically with respect to a center of the pricking component 153.

The lancet body 151 is provided with an element contributing to a mobility prevention of the used lancet or a re-use prevention of the used lancet. Specifically, the lancet body 151 has a recess portion 158 (see FIG. 6(a)) which can cooperate with the flexible locking portion 196 (see FIGS. 3, 8B and 8C) of the lancet engaging part 190. As illustrated in FIG. 6(a), the recess portion 158 is provided by making a part of the lancet body 151 thinner. The recess portion 158 may be positioned at a forward side of the lancet body, for example. In the used lancet assembly, the flexible locking portion 196 of the lancet engaging part 190 can be located in the recess portion 158, and thereby a function of the "re-use prevention" is exerted.

(Lancet Engaging Part)

Figure 7B:
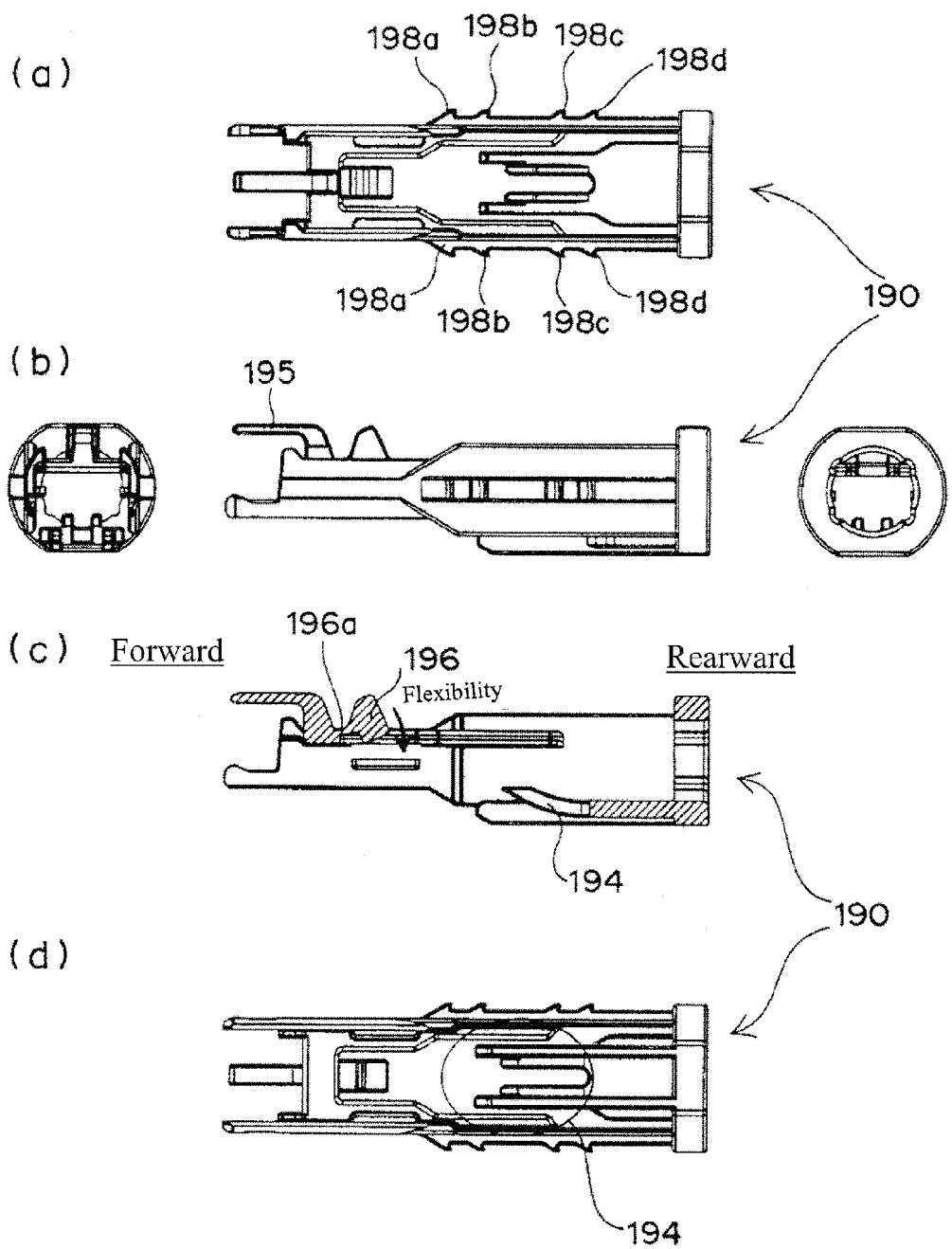
FIGS. 7B(a) through 7B(d) are perspective views illustrating a plane view, a side view and a cross sectional view of the lancet engaging part, respectively.

The lancet engaging part 190 is shown in FIGS. 7A and 7B. As illustrated, the lancet engaging part 190 has a hollow configuration. That is, the lancet engaging part 190 is configured to have a hollow portion 197 around a center axis along a pricking direction. The hollow portion 197 is a space for accommodating the lancet 150. That is, the lancet assembly 100 of the present invention has the lancet engaging part 190 and the lancet 150 assembled together such that the lancet can be positioned within the hollow portion 197 of the lancet engaging part.

As illustrated in FIGS. 7A(a) and 7A(b), the lancet engaging part 190 comprises a pair of cap pressing portions 192 which serve to separate the lancet cap 152 from the lancet. In the lancet assembly 100, the cap pressing portions 192 of the lancet engaging part are capable of making contact with the rear end portions 152a of the lancet cap.

The lancet engaging part 190 has a function of releasing the secured state of the lancet body with respect to the lancet case. Specifically, the lancet engaging part 190 is provided with a disengagement portion 194 which serves to release the engagement/secured state between the engagement portion "A" (110) provided inside the lancet case and the engaged portion "B" (135) of the lancet body (see FIGS. 7B(c) and 7B(d)). As illustrated in FIG. 7B(c), it is preferred that the disengagement portion 194 has a so-called "tweezers" shape. More specifically, it is preferred that the disengagement portion 194 of the lancet engaging part 190 comprises a pair of elongate sections with their tips being curved obliquely forward.

The lancet engaging part 190 comprises a guide 191 (see FIG. 7A) which serves to guide the lancet body (i.e., the "lancet body with the tip of the pricking component exposed") in the pricking direction upon the pricking. It is preferred that the guide 191 is in a form of "continuous raised section" provided on the interior-sided face of the lancet engaging part, as illustrated in FIG. 7A. It is more preferred that the guides 191 have a paired form as a whole. The guide 191 cooperates with the guided component 157 of the lancet body 151 (see FIGS. 6(a) and 6(b)), thereby guiding a movement of the lancet body in the pricking direction. In light of such guide function, the lancet engaging part 190 in itself can also be referred to as "inner guide".

As illustrated in FIGS. 7A(c) and 7B(b), the lancet engaging part 190 preferably comprises an indicator portion 195. As illustrated, the indicator portion 195 may be provided on a forward side of the lancet and is preferably in an elongate form such that it extends forward. The indicator portion 195 functions together with the partial cutout 106 of the lancet case (see FIG. 5(a)). Specifically, the indicator portion 195 can be partially exposed through the partial cutout 106 upon the pricking operation.

The lancet engaging part 190 is also provided with an element contributing to a mobility prevention of the used lancet or to a re-use prevention of the used lancet. Specifically, it is preferred that a flexible locking portion 196 is provided in the lancet engaging part 190 (see FIGS. 7A(c) and 7B(c)). A base 196a of the flexible locking portion 196 has a thinner form as illustrated in FIG. 7B(c). The flexible locking portion 196 can be flexed inwardly around the thinner base 196a serving the axis. As such, when the flexible locking portion 196 of the lancet engaging part abuts against an inner-wall raised portion 180 of the lancet case according to an operation performed after use, the flexible locking portion is forced to be displaced inwardly.

Furthermore, the lancet engaging part 190 is provided with four pairs of projections 198a to 198d which can cooperate with the projections 107 on the inner wall of the lancet case so that the lancet engaging part 190 is suitably secured within the lancet case 102 (see FIG. 7B(a)). That is, the engagement of the four pairs of projections 198a to 198d with the projections 107 (see FIG. 5(c)) of the lancet case allows the lancet engaging part to be suitably secured within the lancet case. This means that the lancet assembled with the lancet engaging part is also suitably secured. At a point in time before the lancet assembly is used, the projections 107 of the lancet case and the projections (198a, 198b) of the lancet engaging part are in an engagement with each other such that each of the projections 107 is disposed between two projections 198a and 198b of the lancet engaging part (see FIG. 8A). On the other hand, at a point in time after the lancet cap is separated and the pricking operation is finished, the projections 107 of the lancet case and the projections (198c, 198d) of the lancet engaging part are in an engagement with each other such that each of the projections 107 of the lancet case is disposed between the two projections 198c and 198d (see FIG. 8B). At a point time after the lancet assembly is ejected from the injector, i.e., after the lancet assembly is used, each of the projections 107 of the lancet case is positioned rearward side of the projection 198d of the lancet engaging part as well as forward side of a rear end portion 199' of the lancet engaging part (see FIG. 8C).

<Functions of Lancet Assembly>

Various unique functions of the lancet assembly of the present invention will be described below. The description about such functions are referred to FIGS. 8A to 8C illustrating change-with-time views of the lancet assembly 100 and FIGS. 9A to 9D illustrating change-with-time views of a pricking device 1000, as appropriate.

(Lancet Cap Removing Mechanism)

Figure 10:
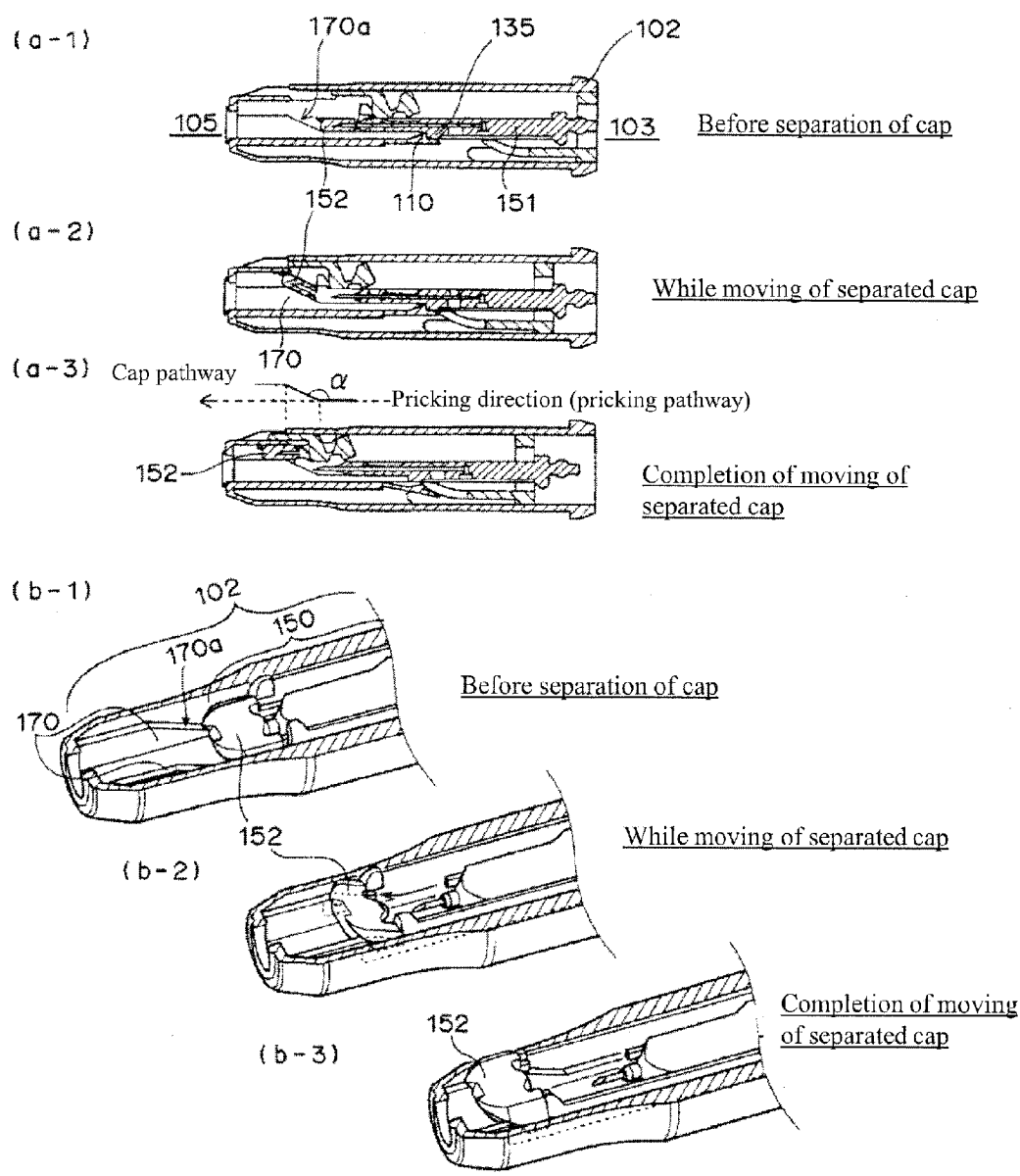
FIG. 10 includes cross sectional views and perspective views for explaining a separation of a lancet cap.

FIG. 10 illustrates the lancet 150 accommodated in the lancet case 102. As illustrated in FIG. 10(a-1), the lancet cap 152 is positioned at the side toward the pricking opening 105 of the lancet case 102, whereas the lancet body 151 is positioned at the side toward the rear opening end 103 of the lancet case 102. As described above, the engagement portion "A" (110) of the lancet case is in contact with the engaged portion "B" (135) of the lancet body, and thus the lancet body 151 is temporarily secured to the lancet case 102 (that is, the forward movement of the lancet body 151 is inhibited). This means that the lancet body 151 is fixed to the lancet case 102, whereas the lancet cap 152 itself is not fixed to the lancet case. Therefore, if only the lancet cap 152 is pressed forward in the pricking direction, a force for departing the lancet cap 152 and the lancet body 151 from each other is generated. Due to this force, the bridging component 154 is broken so that the lancet cap 152 and the lancet body 151 are separated from each other and thereby the tip of the pricking component 153 is exposed.

Subsequently, when the separated lancet cap 152 is pushed in the pricking direction, the cap 152 is forced to be moved forward (see FIGS. 10(a-2) and 10(b-2)). Inside of the lancet case 102 and near the pricking opening 105 thereof, there is provided a slope component 170 for guiding the separated lancet cap 152 to a position that is off the pricking pathway. While on the other hand, the lancet cap 152 is provided with a sloping face 152b (see FIG. 6(b)) having a shape corresponding to the slope component 170. More specifically, it is preferred that the slope component 170 and the sloping face 152b respectively have mutually complementary shape. Owing to the slope component 170 and the sloping face 152b, when the separated lancet cap 152 is forced to be further moved forward, the sloping face 152b of the lancet cap 152 slides while making contact with the slope component 170 provided within the lancet case 102, thus allowing the lancet cap 152 to move to the position that is off the pricking pathway. FIGS. 10(a-1) to 10(a-3) as well as 10(b-1) to 10(b-3) illustrate a state that the separated lancet cap 152 has deviated from the pricking pathway.

The movement of the lancet cap 152 will now be described in more detail. The slope component 170 of the lancet case 102 is provided with a sloped surface 170a angled with respect to the pricking direction (especially see FIG. 10(b-1)). On the other hand, the sloping face 152b of the lancet cap 152 has a surface capable of making complementary contact with the sloped surface 170a (especially see FIG. 6(b) as to the sloping face of the lancet cap). Therefore, when the separated lancet cap 152 is pushed in the pricking direction, the lancet cap 152 slides forward while the sloping face 152b of the lancet cap and the sloped surface 170a of the lancet case are in contact with each other, which result in a forward and oblique movement of the lancet cap. For example, FIGS. 10(a-1) and 10(b-1) illustrate a state before the movement of the separated lancet cap 152. While on the other hand, FIGS. 10(a-3) and 10(b-3) illustrate a state after the movement of the separated lancet cap 152. From an embodiment wherein the lancet cap 152 moves from the position shown in FIGS. 10(a-1) and 10(b-1) to the position shown in FIGS. 10(a-3) and 10(b-3), it will be understood that the lancet cap 152 moves to the position that is off the pricking pathway. A moving path of the lancet cap 152 is illustrated in FIG. 10(a-3). This moving path indicates that the lancet cap 152 eventually deviates from the pricking pathway of the pricking component 153. The angle of the sloped surface 170a with respect to the pricking direction (i.e., an angle α of the moving path of the lancet cap) is preferably in the range of 120° to 150°, more preferably in the rang of 130° to 140°.

Since the lancet cap 152 moves forward in an oblique direction to deviate from the pricking pathway as described above, the pricking component 153 (more specifically, the lancet body 151 with the pricking component 153 exposed) can be launched forward without being obstructed by the lancet cap 152. FIG. 9B(d) schematically shows the lancet assembly 100 upon pricking (namely at the time when the pricking component is being launched). As will be seen from FIG. 9B(d), the tip 153a of the pricking component 153 is protruding from the pricking opening 105 without being obstructed by the lancet cap 152.

When the lancet assembly 100 is loaded into the injector 200 for use, the assembly 100 is inserted through the front end opening 202 of the injector 200 rearward (in the direction indicated by arrow A) as shown in FIG. 9A(a). This loading operation is carried out by holding the lancet case 102 with one hand and then inserting the lancet case 102 through the front end opening 202 of the injector 200 while still holding the injector 200 with the other hand. The loading is complete when the lancet case 102 cannot be further inserted by the force exerted by an ordinary person. The state when loading has been completed is shown in FIG. 9B(c). By carrying out the loading operation, the plunger 204 of the injector 200 is retracted and thereby the force required for launching the pricking component 153 is stored in the plunger. The retracting of the plunger is accompanied by the following actions:

(1) The bridging component is broken so that the lancet cap 152 is separated from the lancet body 151; and then
(2) The separated lancet cap 152 moves and deviates from the pathway of the pricking.

(Disengagement Mechanism of Lancet Body)

Before the separation of the lancet cap 152, the lancet body is secured to the lancet case 102 such that the forward movement of the lancet body 151 is inhibited. While on the other hand, after the separation of the lancet cap 152, the secured state of the lancet body is preferably released. The releasing of the secured state allows the lancet body (specifically, the "lancet body with the tip of the pricking component being exposed") to be launched in the pricking direction for the pricking. Specifically, it is preferred that, at a point in time before the separation of the lancet cap from the lancet body, the mutual engagement between the engagement portion "A" (110) of the lancet case and the engaged portion "B" (135) of the lancet body serves to inhibit the forward movement of the lancet body 151. On the other hand, at a point in time after the separation of the lancet cap 152, such mutual engagement therebetween is released, i.e., the disengagement is performed (see FIGS. 5(d) and 6(b) regarding the engagement portion "A" (110) and the engaged portion "B" (135), for example).

The disengagement will now be described in more detail. FIG. 8A illustrates the lancet assembly 100 before being used (i.e., at a point in time before the cap is separated). As illustrated in FIG. 8A, at a point in time before the separation of the cap, the engagement portion "A" (110) of the lancet case and the engaged portion "B" (135) of the lancet body are in engagement with each other such that the engagement portion "A" (110) is positioned at the forward side with respect to the engaged portion "B" (135), i.e., the engaged portion "B" (135) is positioned at the rearward side with respect to the engagement portion "A" (110). As a result, the forward movement of the lancet body 151 is inhibited. In other words, if the lancet cap 152 is pressed forward upon the separation of the cap, a force for resisting such pressing is applied to the lancet body 151, which causes the lancet body and the lancet cap to be subjected to forces for moving them away from each other. Such forces for moving the lancet body and the lancet cap away from each other eventually bring the separation of the lancet cap from the lancet body.

Figure 11:
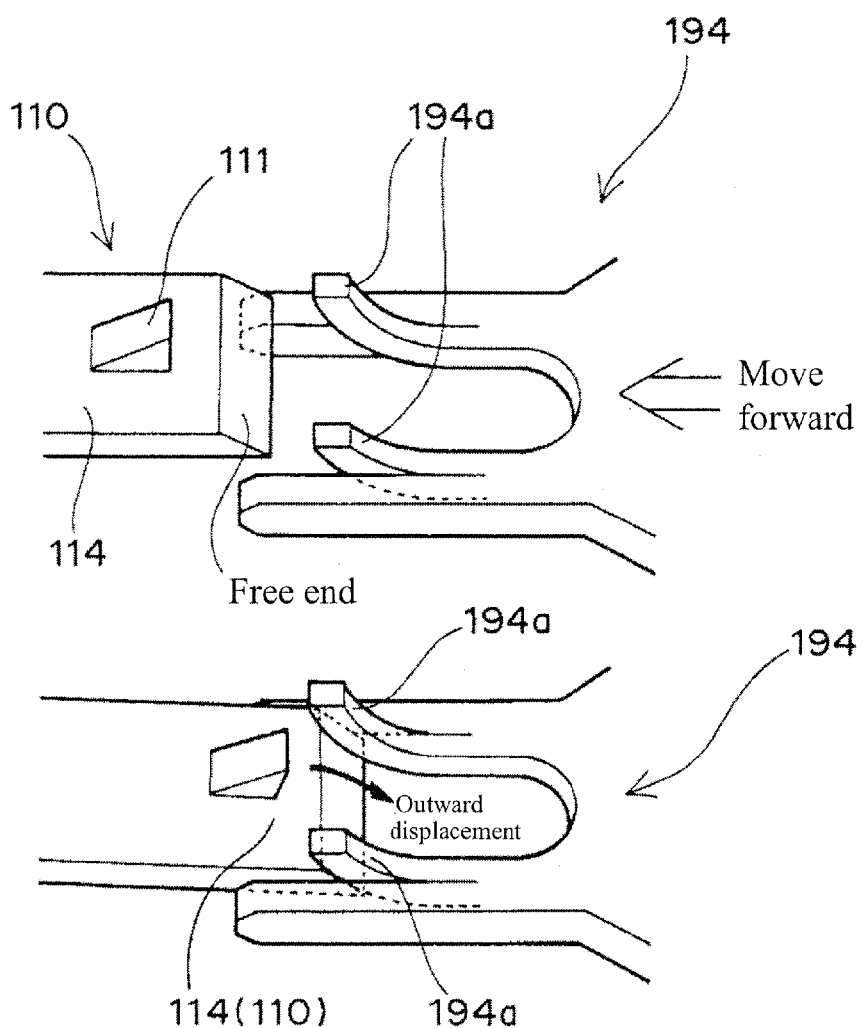
FIG. 11 includes schematic perspective views for explaining a releasing of an engagement between an engagement portion "A" of the lancet case and an engaged portion "B" of a lancet body.

FIG. 8B illustrates the lancet assembly 100 after the separation of the cap. As illustrated in FIG. 8B, at a point in time after the separation of the lancet cap, the disengagement portion 194 of the lancet engaging part 190 serves to release the mutual engagement between the engagement portion "A" (110) of the lancet case 102 and the engaged portion "B" (135) of the lancet body. 151. As illustrated in FIG. 11, the disengagement portion 194, which is forced to be moved forward, serves to displace the engagement portion "A" (110) of the lancet case outwardly, thereby releasing the mutual engagement between the engagement portion "A" (110) of the lancet case and the engaged portion "B" (135) of the lancet body. More specifically, the pair of elongate curved sections 194a which extend obliquely forward, which is provided in the disengagement portion 194, abut against the free end of the elongated section 114 of the engagement portion "A" (110). As a result, the elongated section 114 is forced to be displaced flexibly and outwardly by the pair of elongate curved sections 194a, which leads to a disengagement between the projection 111 of the engagement portion "A" of the lancet case and the engaged portion "B" (135) of the lancet body. After the disengagement, the "lancet body with the tip of the pricking component being exposed" can be ready for launching movement in the pricking direction for the pricking.

(Indicator Function)

According to a preferred embodiment of the present invention, the lancet assembly has an indicator function. Such indicator function is provided for indicating that the lancet assembly combined with the injector becomes ready for pricking. The "elongated indicator portion 195 extending forward" (see FIG. 7B(b)) provided in the lancet engaging part 190 and the "partial cutout 106" (see FIG. 5(a)) provided in the lancet case 102 are main members/parts which contribute to the indicator function of the lancet assembly.

In the "lancet assembly 100 before being used (i.e., before the separation of the cap)", the indicator portion 195 of the lancet engaging part is located at such a position that the indicator portion 195 cannot be seen from the partial cutout 106 of the lancet case 102, as illustrated in FIG. 8A. Specifically as illustrated in FIG. 8A, the indicator portion 195 is located at a retracted position from the partial cutout 106, and thus the indicator portion 195 before the lancet assembly is used is not exposed from the partial cutout 106 (see FIG. 12 as well as FIG. 8A).

Figure 12:
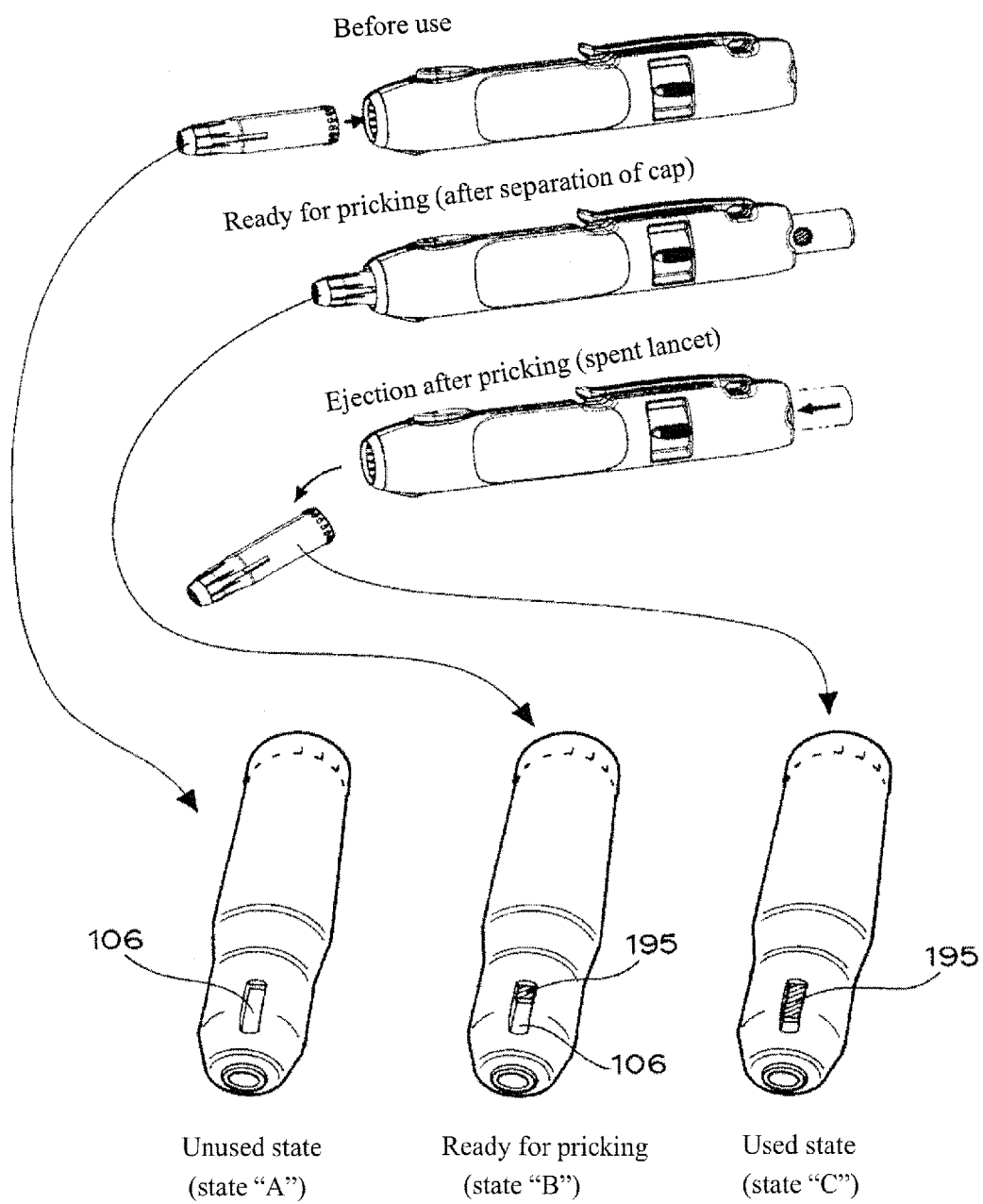
FIG. 12 includes schematic perspective views for explaining an indicator function.

While on the other hand, at a point in time after the cap is separated, the indicator portion 195 of the lancet engaging part is located so as to be partially exposed from the partial cutout 106 of the lancet case 102 as illustrated in FIG. 8B (see, FIG. 12 as well as 8B). This is due to the forward movement of the lancet engaging part 190 within the lancet case upon the separation of the lancet cap. The movement of the lancet engaging part 190 is related to the separation/movement of the lancet cap 152. Accordingly, the separation of the lancet cap can be indirectly recognized from an exposure state of the indicator portion 195 of the lancet engaging part 190. It can be thus recognized whether or not a power necessary for launching the pricking component is stored in the plunger to the level at which the pricking component is ready for pricking. In other words, the state "B" of the indicator portion 195 as shown in FIG. 12 indicates that the lancet assembly loaded into the injector is ready for pricking. As such, the lancet assembly of the present invention makes it possible to indirectly recognize a state inside the case from the outside, so that the user can securely recognize which operation steps the lancet assembly is now undergoing. This contributes to a smooth operation of the lancet assembly.

Furthermore, at a point in time after the pricking is performed and then the lancet assembly is ejected from the injector, i.e., after the lancet assembly is used, the indicator portion 195 of the lancet engaging part is located so as to be further exposed from the partial cutout 106 of the lancet case 102 as illustrated in FIG. 8C (see FIG. 12 as well as FIG. 8C). This is due to the further forward movement of the lancet engaging part 190 within the lancet case upon the ejection of the lancet assembly from the injector. From the exposed state of the indicator portion 195, it can be recognized whether or not the lancet assembly has been already used for the pricking. In other words, the state "C" as shown in FIG. 12 (i.e., the exposed state "C" of the indicator portion 195) indicates that the lancet assembly is the used one ejected from the injector after being used and thus can be no longer used for pricking. Such indicator function according to the present invention can reduce a risk of erroneous use of the used lancet assembly.

(Safety Function and Re-Use Prevention Function)

According to a preferred embodiment of the present invention, the lancet assembly has a "function of preventing the used pricking component from coming off the case", i.e., "re-use preventing function for preventing the used lancet from being used again". Main components or parts contributing to such functions are the "flexible locking portion 196 capable of being inwardly flexed (see FIG. 7A(c))" provided on the lancet engaging part 190, the "internal raised portion 180 which projects toward the center of the case (see FIG. 5(c))" provided on the lancet case 102, and the "recess portion 158 in a form of a partially thin portion of the lancet (see FIG. 6(a))" provided on the lancet body 151.

In the used lancet assembly at a point in time after the pricking, the flexible locking portion 196 and the internal raised portion 180 of the lancet case 102 are located side by side, but the flexible locking portion 196 is not in an abutment against the internal raised portion, as illustrated in FIGS. 13(a) and 8B. That is, in such a state, the flexible locking portion 196 of the lancet engaging part is not yet displaced and thus is not in an engagement with the lancet body 151. When the lancet engaging part is forced to be moved forward from such a state (i.e., the lancet engaging part is forced to be moved forward according to the case ejection operation), the internal raised portion 180 serves to displace the flexible locking portion 196, which eventually allows the flexible locking portion 196 to engage with the lancet body 151 (see FIGS. 13(b) and 8C).

Specifically, when the lancet assembly after the pricking is ejected from the injector, the lancet engaging part 190 is pressed by the ejector to be moved forward within the lancet case 102 (see FIGS. 8B, 8C, 9C(e), and 9C(f)). The forward movement of the lancet engaging part 190 involves the forward movement of the flexible locking portion 196 equipped therewith. When the flexible locking portion 196 of the lancet engaging part is forced to be moved forward with respect to the lancet case 102, the flexible locking portion 196 can abut against the inner-wall raised portion 180 of the lancet case, and thereby the flexible locking portion 196 is forced to be displaced inwardly. The flexible locking portion 196 thus displaced results in being located in the recess portion 158 of the lancet body 151 (see FIGS. 13(b), 8C, and 9C(f)). After the displaced locking portion 196 is located in the recess portion 158, the movement/behavior of the lancet body 151 in itself is limited by such locking portion 196. This means that the used lancet after the pricking will not come off the case. Therefore, the safeness and the hygiene of the used lancet assembly can be improved. Further, since the lancet body cannot move any more due to the displaced locking portion, the lancet body cannot be re-used for the pricking. As a result, the used lancet assembly ejected from the injector is not re-usable.

<Entire Structure and Functions of Injector>

Figure 14B:
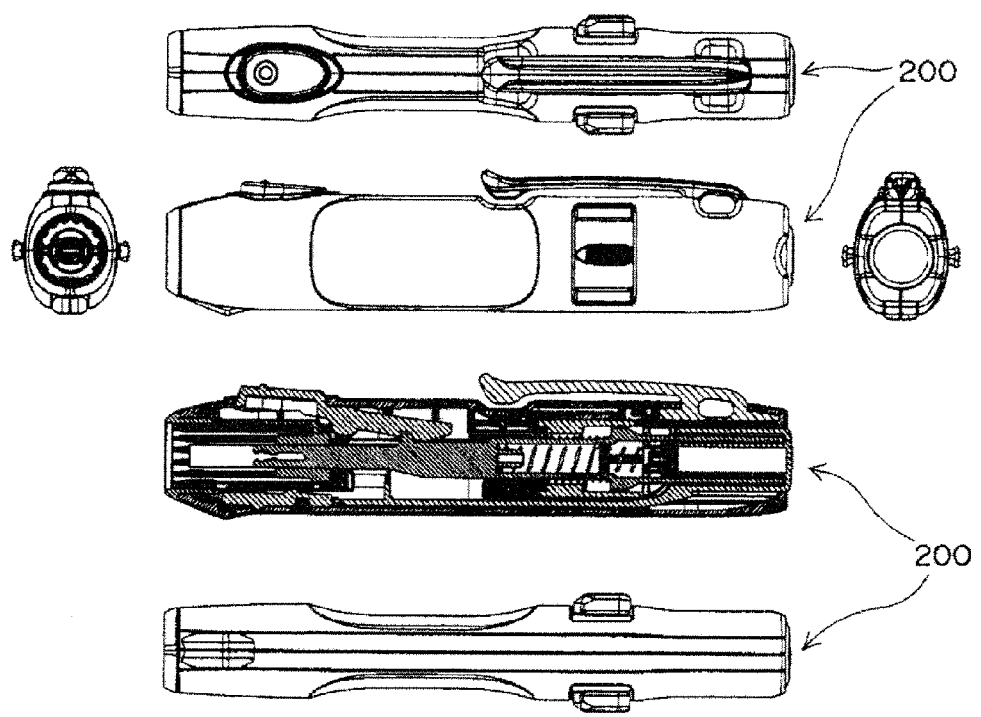
FIG. 14B includes appearance views and cross sectional views of the injector.
Figure 14C:
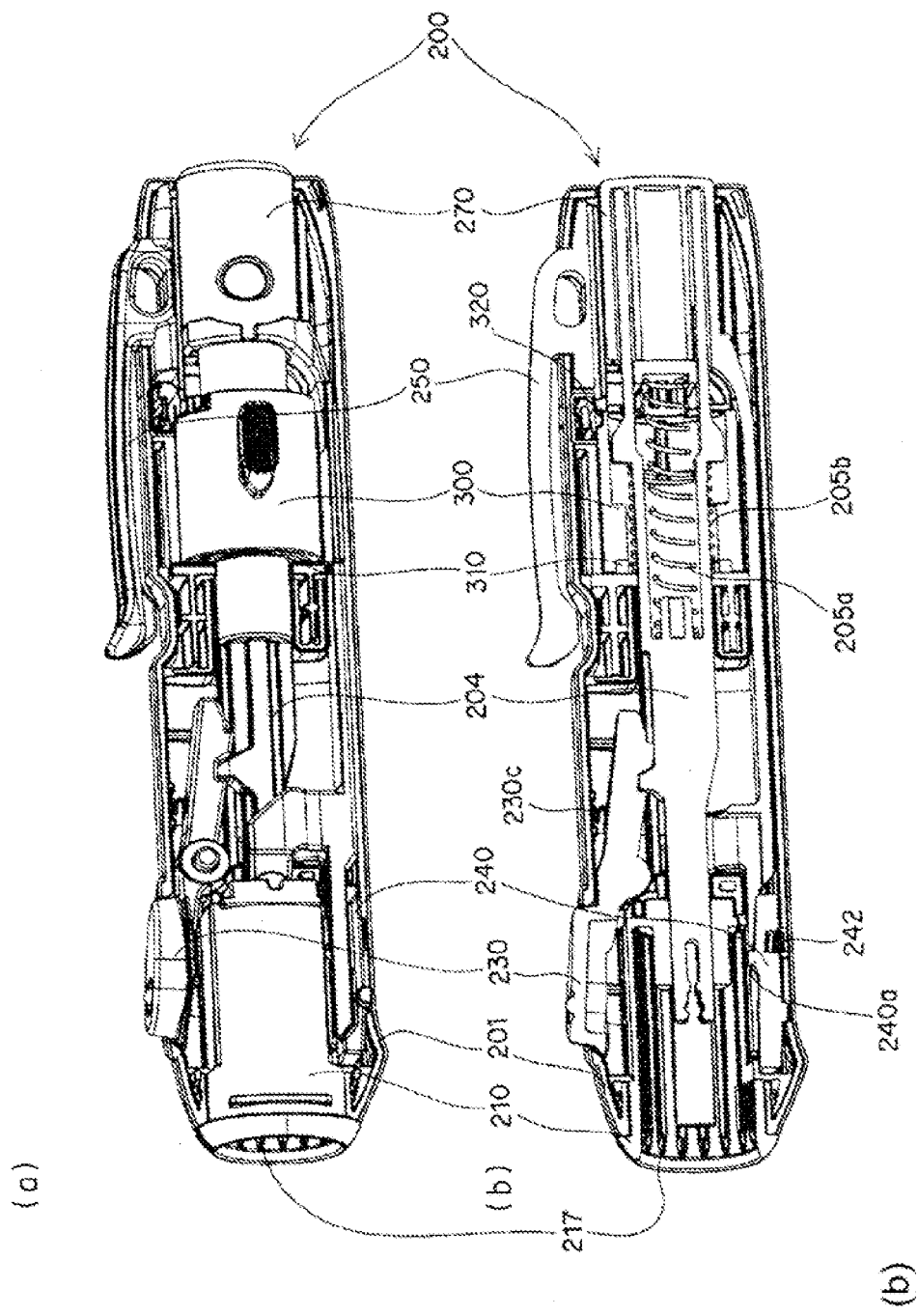
FIGS. 14C(a) and 14C(b) are perspective views illustrating an internal structure of the injector.

FIGS. 14A to 14C illustrate an injector 200 according to the present invention. FIG. 14A includes appearance views of the injector 200. FIGS. 14B and 14C illustrate side faces and internal structures of the injector 200. As illustrated in FIG. 14C, the injector 200 comprises a housing 201, a plunger 204, and a lancet assembly receiving part 210. The injector 200 may further comprise, in addition to the above, a trigger lever 230, an ejector 270, a fire spring (i.e., an ejection spring) 205a, a return spring 205b, a case locking part 240, a hook 250, an adjuster (i.e., a pricking depth adjustment part) 300, and an adjuster ring 310. The above described components are illustrated in FIGS. 15(a) to 15(c), FIGS. 16(a) to 16(d), and FIGS. 17(a) to 17(d).

The housing 201 of the injector 200 is preferably composed of halved members. For example, a member 201a and a member 201b as shown in FIG. 15(a) are integrally combined to form the housing 201.

The plunger 204 is disposed along the longitudinal direction of the injector 200. The plunger 204 has a function of launching the lancet body 151 in the pricking direction. As shown in FIG. 9A and FIG. 15(b), a front end portion 204a of the plunger 204 is configured to engage with a rear end portion 165 (see FIG. 6(b)) of the lancet body 151. By inserting the lancet body 151 into the injector 200 upon loading the lancet assembly 100 into the injector 200, the front end portion 204a of the plunger 204 engages with the rear end portion 165 of the lancet body 151. As the lancet body 151 is inserted further rearward, the plunger 204 is thrust backward. As a result, the fire spring 205a (see FIG. 14C) provided on the plunger 204 is compressed. This means that a force required for launching the pricking component 153 can be stored in the plunger 204.

(Lancet Assembly Receiving Part)

Figure 18:
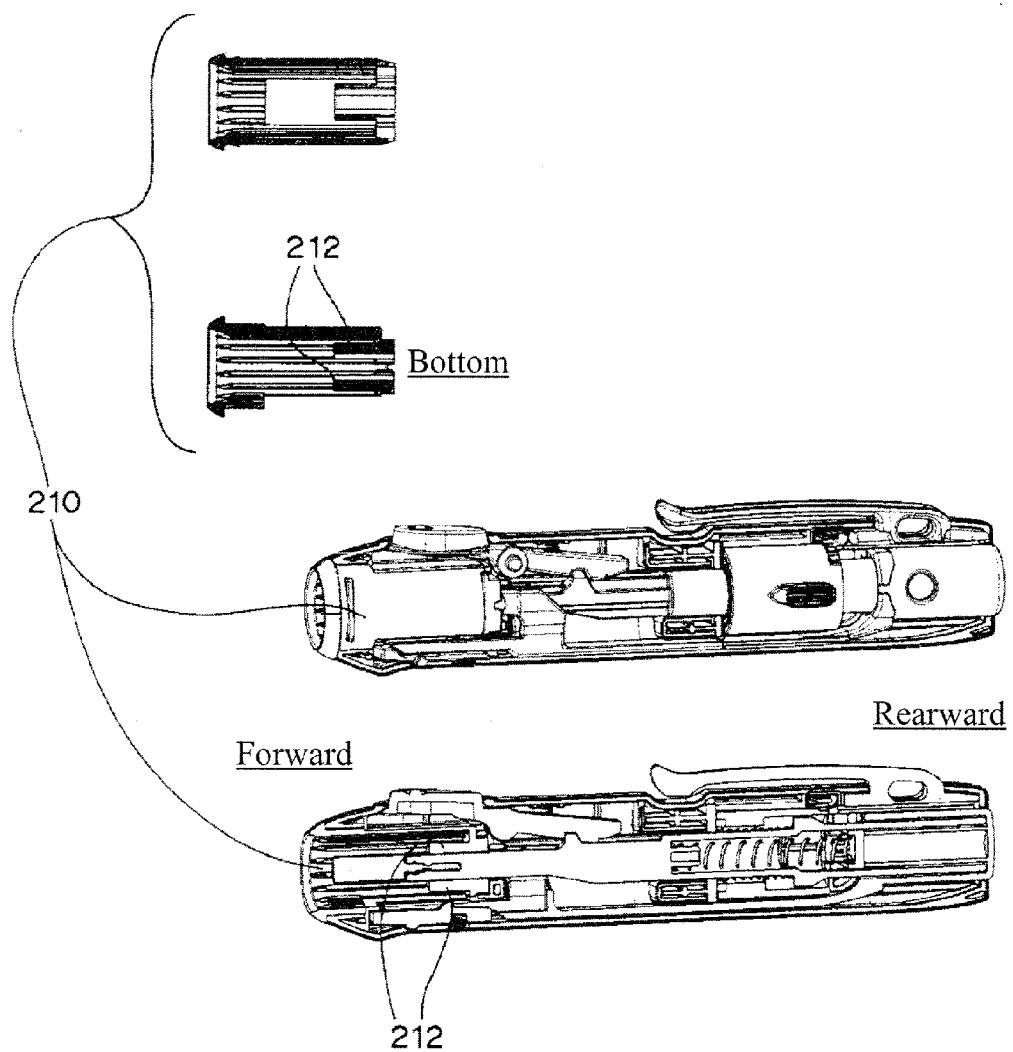
FIG. 18 includes perspective views illustrating the lancet assembly receiving part.

The injector 200 of the present invention comprises a lancet assembly receiving part 210. The lancet assembly receiving part 210 has a function of accommodating the lancet assembly during its use as well as contributing to the removal of the cap upon loading of the lancet assembly. The lancet assembly receiving part 210 has a cylindrical shape or a ring shape as a whole. As illustrated in FIG. 18, the lancet assembly receiving part 210 is equipped with forward projecting portions 212 in the interior thereof. As illustrated, each of the forward projecting portions 212 extends forward from a bottom portion of the receiving part 210. Preferably, the forward projecting portions 212 are formed so as to "be paired".

The receiving part 210 in itself is provided at a front end opening of the injector as illustrated in FIG. 18 so as to receive the lancet assembly upon the insertion thereof for use. In other words, the receiving part 210 has such a configuration that the lancet assembly can be loaded into the injector in such a manner that the lancet case is partially accommodated within the receiving part 210. During the loading operation of the injector 200 wherein the lancet assembly is inserted into the receiving part 210, the lancet engaging part 190 is subjected to a force for causing the lancet engaging part 190 to be moved forward due to the existence of the forward projecting portions 212. Especially, there can be generated the force forcing the lancet engaging part 190 to be moved forward with respect to the lancet case. More specifically, when the "lancet assembly with the forward movement of the lancet body being inhibited" is inserted into the receiving part 210, a rear end portion 199 of the lancet engaging part comes to contact with the forward projecting portions 212 of the assembly receiving part 210 (see FIGS. 9A(a) and 9A(b), for example). As the lancet case 102 is further inserted, the lancet case 102 is pushed by the forward projecting portions 212 to force the lancet engaging part 190 to be moved forward within the lancet case (see for example FIG. 9B(c)). In other words, due to the contact between the rear end portion 199 of the lancet engaging part (especially the lancet engaging part which has been inserted into the injector) and the forward projecting portions 212 of the receiving part 210, the "force causing the lancet engaging part to be moved forward with respect to the lancet case" is generated in the lancet engaging part. Consequently, the lancet cap is pushed by the pressing portions 192 of the lancet engaging part, resulting in a separation of the lancet cap from the lancet body and also a movement of the separated cap to a position off the pricking pathway (see FIG. 10).

An inner surface of the lancet assembly receiving part 210 is provided with guiding projections 217 (see FIGS. 14A and 14C). More specifically, the inner surface of the receiving part 210 is provided with the plurality of the guiding projections 217 which are respectively continuously raised along the inserting direction. The guiding projections 217 cooperate with the plurality of projections 104 (see FIG. 5(b)) provided on the outer surface of the lancet case during the loading the lancet assembly 100, and thereby promoting a smooth insertion of the lancet assembly into the case. As long as the guiding projections 217 of the receiving member cooperate with the projections of the case, the lancet assembly can be inserted into the injector in any rotational orientation (i.e., the rotational orientation around the central axis is not limited). Thus, the lancet assembly of the present invention is excellent in an operability in use (i.e., there is provided a largely reduced limit of the insertion orientation of the lancet assembly).

(Case Lock Function)

The injector 200 of the present invention preferably has a case lock function. The case lock function prevents the lancet assembly to come off the injector. Specifically, the lancet assembly can be retained in the injector even when the lancet assembly is applied with a force in a direction opposite to the insertion direction at a point in time after the insertion of the lancet assembly into the injector is completed. Main components or parts contributing to such functions are the "case locking part 240 (see FIGS. 14C and 17(a))" and the "projections 104 (see FIG. 5(b))" provided on the outer surface of the lancet case.

Figure 19:
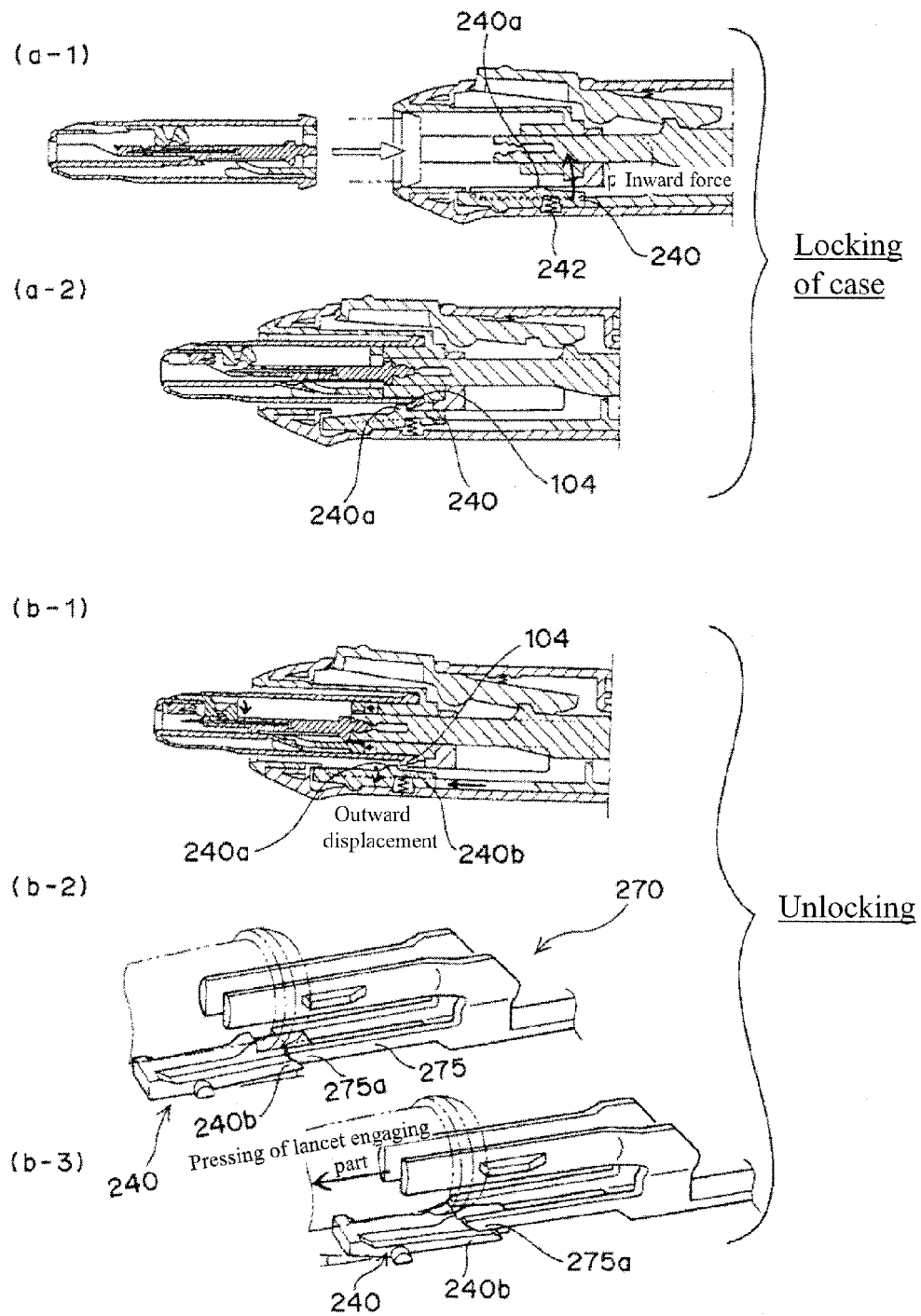
FIG. 19 includes schematic views for explaining "case locking" and "unlocking".

As illustrated in FIG. 19(a-1), the case locking part 240 comprises a stopper 240a which projects toward the inside of the injector (see also FIG. 17(a)). A spring 242 is provided between the case locking part and a sidewall of the housing of the injector, and thereby an inward force toward the inside of the injector is applied to the case locking part 240. When the lancet assembly 100 is inserted into the injector 200 equipped with the case locking part 240, the projection 104 of the lancet case 102 slides on the case locking part 240. When the lancet assembly 100 is further inserted into the injector 200, the projection 104 of the case locking part 240 rides over the stopper 240a. The inward force is applied to the case locking part 240 due to the spring 242. Thus, upon the sliding and riding of the projection 104 on the stopper 240a, the projection 104 allows the locking part 240 to displace outwardly against the action of the spring 242 (the displacement of the locking part is performed around the position of the spring 242). After the projection rides over the stopper, the case locking part 240 is returned to its original position. Therefore, at a point in time after the projection 104 of the case rides over the stopper 240a, the projection 104 and the stopper 240a are capable of making contact with each other (see FIG. 19(a-2)). This can prevent the lancet case from coming off the injector.

(Ejector Function)

The injector 200 has an ejector function. The ejector function makes it possible to eject the lancet case 102 from the injector 200 after the pricking. An ejector 270 provided in the injector 200 is used for ejecting the loaded lancet assembly. As illustrated in FIG. 16(b), the ejector 270 is preferably in a form of an elongate ejector as a whole. In other words, the ejector 270 preferably has an elongated shape as a whole such that it extends longwise. A rear end portion of the elongate ejector 270 is provided with a force point 272 on which a force for a forward movement thereof can be applied. The force point 272 provided at the rear end portion of the elongate ejector 270 can be exposed from the housing of the injector (see FIGS. 20 and 9C(f), 9D(g), for example).

Figure 20:
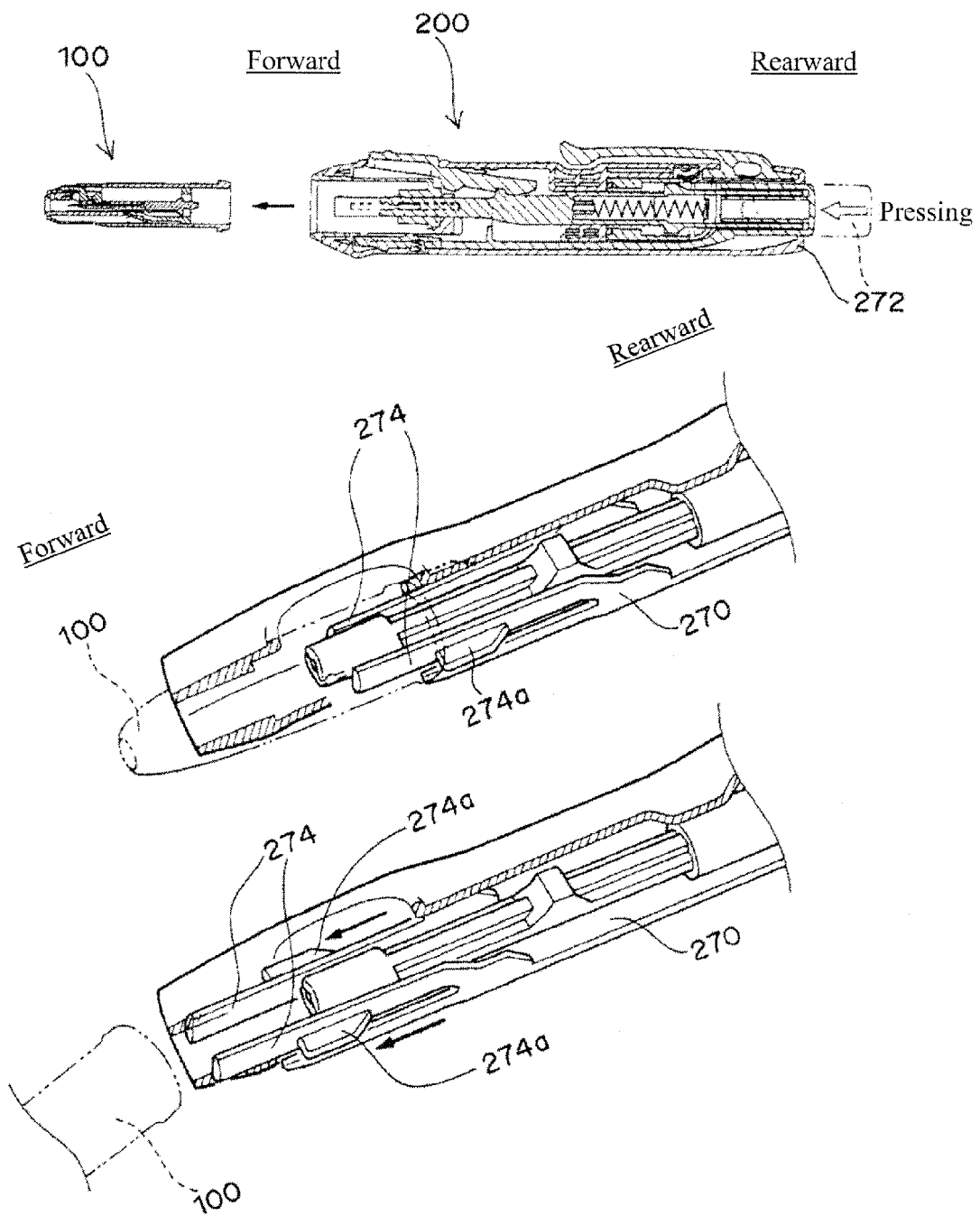
FIG. 20 includes schematic views illustrating for explaining a pressing of the ejector.

When the user applies a forward force to the force point 272 of the rear end portion of the ejector to press it forward, the ejector 270 is forced to be moved forward as a whole (see FIG. 20). This enables the front end portion 274 of the ejector to make contact with a portion 199' of the lancet engaging part (i.e., the portion 199' which is different from the portion 199 with which the forward projecting portions 212 of the lancet assembly receiving part make contact (see FIG. 8C). As a result thereof, the front end portion 274 of the ejector makes it possible to push the lancet engaging part. Therefore, when the ejector is forced to be further moved forward after the contact of the ejector, the lancet engaging part 190 can be moved forward within the lancet case. The forward end portion 274 of the ejector may be provided with wing portion 274a for stabilize a pressing operation (see FIG. 20). The wing portion 274a makes contact with the inner wall portion of the injector/housing (or the raised portion which projects from the inner wall portion of the housing) during the forward movement of the ejector, and thereby the ejector (specifically, the front end portion 274 of the ejector) can act against the force given from the lancet engaging part 190.

The lancet engaging part 190 which has been moved forward is finally located at the most forward position in the lancet case. This means that the front end portion 193 of the lancet engaging part finally makes contact with the inner wall portion of the lancet case (see FIG. 8C). Accordingly, when the user attempts to force the lancet engaging part to be further moved forward by pressing the ejector, the lancet case is pushed forward by the lancet engaging part, which leads to a forward pressing of the lancet assembly as a whole. Therefore, when the ejector is continuously moved forward, the lancet assembly is finally ejected from the injector.

(Unlocking Function)

The case locking can be released upon the ejection of the lancet assembly from the injector. In this regard, an unlocking portion 275 (see FIG. 16(b)) of the ejector 270 serves to release the case locking. More specifically, when the ejector is forced to be moved forward after the pricking, the unlocking portion 275 of the ejector 270 abuts against a rear end edge 240b of the case locking part as illustrated in FIGS. 19(b-1) to 19(b-3). This causes the case locking part 240 to be displaced outwardly to release the case locking. More specifically, the tip 275a of the unlocking portion 275, which is being moved forward, serves to press the rear end edge 240b of the case locking part outwardly, so that the case locking part 240 is displaced outwardly around the spring portion 242 of the case locking part 240. As a result thereof, the stopper 240a of the locking part and the case are not any longer capable of making contacting with each other.

(Embodiment in Use)

With reference to FIGS. 9A(a) to 9D(g), the procedures of operation will now be described serially from the loading of the lancet assembly 100 through the completion of loading and pricking until the ejection of the spent lancet assembly 100 after pricking. FIGS. 9A(a) to 9D(g) illustrate the time changes of the lancet assembly 100 and the injector 200 (i.e., time changes of the pricking device) in the sequential order of the figure numbers.

First, as illustrated in FIG. 9A(a), the lancet assembly 100 and the injector 200 are prepared. Then, the lancet case 102 is inserted into the injector 200 through the front end opening 202 of the injector 200 to start the loading of the lancet assembly 100. In this loading, the lancet case 102 is inserted such that the pricking opening 105 of the lancet case 102 is oriented forward as illustrated in FIG. 9A(b). In other words, the lancet case 102 is inserted into the receiving part 210 of the injector 200 from an open end 103 of the lancet case 102.

When the lancet assembly 100 is inserted, the rear end portion 199 of the lancet engaging part makes contact with the forward projecting portions 212 of the lancet assembly receiving part 210 as illustrated in FIG. 9B(c). Due to the contact of the lancet engaging part 190 with the forward projecting portions 212, the lancet engaging part 190 is pushed by the forward projecting portions 212, and thereby the lancet engaging part 190 is forced to be moved forward within the lancet case. Prior to the contact between the lancet engaging part 190 and the forward projecting portions 212, the lancet body 151 makes engagement with the plunger 204 as illustrated in FIG. 9A(b). Therefore, when the lancet case 102 is further inserted thereafter, the lancet body 151 secured to the lancet case 102 acts to push the plunger 204 rearward, and thereby the plunger 204 is retracted. The retraction of the plunger 204 by the rear end portion of the lancet body 151 is performed while resisting the force of the fire spring 205a. Thus, the retracted plunger eventually causes the spring 205a of the plunger 204 to be compressed and thereby the force required for launching the pricking component 153 is stored in the plunger 204. The retracting of the plunger is performed until a trigger projection 204b of the plunger 204 makes engagement with a rear stepped portion 230a of a trigger lever 230 to be placed in a cocking state (see FIG. 9B(c)). After the plunger is retracted to be placed in the cocking state, a rear end portion 204c of the plunger comes to be exposed from a partial cutout 272a of the rear end portion (i.e., the force point 272) of the ejector (see FIGS. 9B(c), 15(b) and 16(b)), and thereby it can be visually recognized whether or not the lancet assembly is ready for pricking.

The forward movement of the lancet body 151 is inhibited, whereas the lancet cap 152 in itself is not retained. Thus, the lancet engaging part "pushed" by the forward projecting portions 212 forces the lancet cap 152 to be effectively pressed. This brings about a force for moving the lancet cap 152 and the lancet body 151 away from each other, so that a bridging component 154 connecting between the lancet cap 152 and the lancet body 151 is finally broken. When the bridging component 154 is broken, the lancet cap 152 is separated from the lancet body 151, and thereafter the separated lancet cap 152 is forced to be moved to reach the position off the pricking pathway (FIG. 9B(c) illustrates a state that the cap 152 has been positioned off the pricking pathway). After the separation of the cap, the disengagement portion 194 of the lancet engaging part can function to release the engagement between the engagement portion "A" (110) of the lancet case and the engaged portion "B" (135) of the lancet body (see FIG. 8B).

The loading of the lancet assembly by inserting the lancet case 102 into the injector 200 is completed through the following steps (i) to (v):

(i) The lancet cap 152 is separated from the lancet body 151, so that the tip of the pricking component 153 is exposed whereas the pricking component 153 remains situated in the lancet body 151;

(ii) The separated lancet body 151 is forced to be moved to the position off the pricking pathway;

(iii) The plunger is retracted;

(iv) The projection 204b of the plunger 204 and the rear stepped portion of the trigger lever 230 becomes in a cocked state; and (v) The lancet body 151 is no longer secured to the lancet case 102, which results in a completion of the loading operation.

Figure 21:
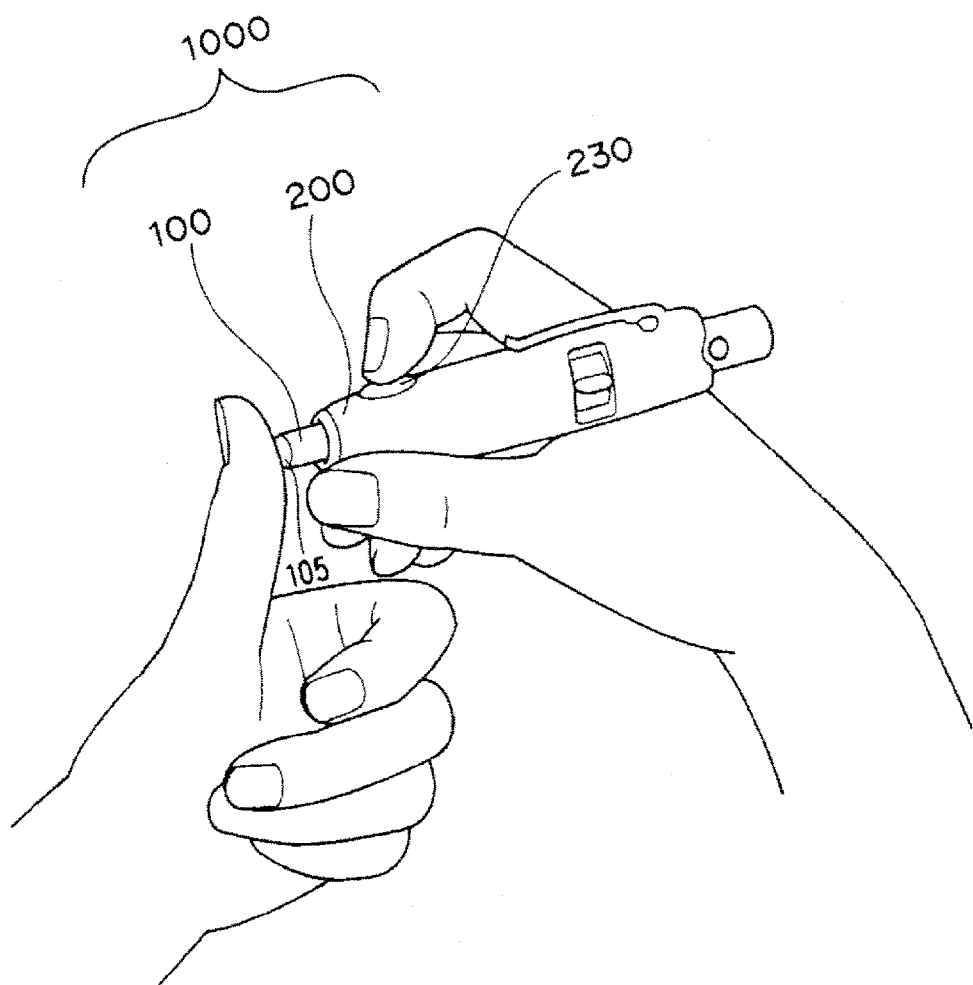
FIG. 21 schematically illustrates a pricking device during its use.

Subsequently, the pricking is performed as follows: the pricking opening 105 is applied to a predetermined region to be pricked (for example, a finger tip). Then, the trigger lever 230 is pushed toward the inside of the injector (see FIG. 21) so as to cease the engagement (i.e., contact) between the rear stepped portion 230a of the trigger lever 230 and the projection 204b of the plunger 204. This results in an instantaneous expansion of the compressed spring 205a, and thereby the lancet body 151 is launched in the pricking direction. FIG. 9B(d) illustrates the state immediately after the trigger lever 230 is pressed toward the inside of the injector 200 to launch the lancet body with the tip of the pricking component exposed.

Upon the launching of the lancet body 151, the lancet body 151 is guided by an inner guide of the lancet engaging part to be moved forward in the pricking direction. Specifically, the cooperation between the guide 191 (see FIG. 7A) of the lancet engaging part 190 and the guided components 157 (see FIGS. 6(a) and 6(b)) of the lancet body 151 enables a suitable launching of the lancet body in the pricking direction. Upon the pricking, the fire spring 205a expands as much as possible whereas the return spring 205b is compressed. Therefore, after the predetermined region is pricked by the pricking component, the fire spring 205a attempts to recover its original form whereas the compressed return spring 205b also attempts to recover its original form, so that the plunger 204 is subjected to a rearward force. As a result thereof, the lancet body 151, i.e., the pricking component 153, can be swiftly retracted immediately after the pricking. FIG. 9C(e) illustrates the state after pricking.

In order to eject the lancet case 102 (more specifically, the used lancet assembly 100) from the injector 200 after pricking, the ejector 270 of the injector 200 is activated. More specifically, a force from the outside is applied to the force point 272 of the rear end portion of the ejector 270. As a result, the lancet engaging part 190 is forced to be moved forward and thereby the unlocking function of the ejector 270 is provided.

The lancet engaging part 190, which is forced to be moved forward due to the activation of the ejector, is finally located at the most forward position within the lancet case. In other words, the lancet engaging part 190 is forced to be moved forward to such a position that the forward end portion 193 of the lancet engaging part makes contact with the inner wall portion of the lancet case (see FIG. 8C). After such contact, the ejector is further pushed to cause the lancet engaging part to be moved forward, and thereby the lancet case is pushed forward by the lancet engaging part. As a result, the lancet assembly as a whole is pressed forward. The continuous forward movement of the ejector results in causing the lancet assembly to be moved forward as a whole, which leads to an achievement of the ejection of the lancet assembly from the injector. With respect to the ejection, the flexible locking portion 196 is displaced to make engagement with the lancet body 151 (see FIG. 9C(f)), and thus the movement of the lancet body 151 in itself comes to be inhibited within the case. This can prevent the lancet assembly from becoming ready for pricking again. In other words, even if the ejected used lancet assembly is loaded into the injector again, the lancet body cannot become in the movable state so that the used lancet assembly cannot become ready for pricking.

The lancet case 102 thus ejected accommodates therein the lancet body 151 from which the tip of the pricking component 153 is exposed. In the lancet assembly after being used and thus ejected from the injector, the lancet body is located at the most forward position within the lancet case, compared with the position thereof before being used. As a result thereof, even if the used lancet assembly is loaded into the injector, the rear end portion of the lancet body and the plunger of the injector cannot make engagement with each other due to their positions. More specifically, due to the fact that a distance "L1" is larger than a distance "L2" in FIG. 9D(g), even if the used lancet assembly is loaded into the injector, the rear end portion of the lancet body will not be able to reach a locking portion provided at the tip of the plunger. As such, the lancet assembly is prevented from being re-used. More specifically, even if the used lancet assembly of the present invention is loaded into the injector, the plunger cannot be retracted effectively, and thereby the lancet assembly cannot become ready for pricking any more.

It should be noted that the present invention as described above includes the following aspects.

The first aspect: A lancet assembly comprising:
- a lancet;
- a lancet engaging part; and
- a lancet case housing the lancet and the lancet engaging part, wherein
- the lancet comprises a lancet body, a lancet cap and a pricking component, the lancet body and the lancet cap being made of resin and the pricking component being made of metal, the pricking component is disposed in both the lancet body and the lancet cap, the tip of the pricking component is covered with the lancet cap, and the lancet cap and the lancet body are integrally connected together by a bridging component;
- the lancet engaging part and the lancet cap are disposed such that the lancet engaging part and the lancet cap are capable of making contact with each other;
- when the lancet engaging part is forced to be moved forward with respect to the lancet in a pricking direction, the lancet cap is pressed by the lancet engaging part, and thereby the bridging component is broken so that the lancet cap is separated from the lancet body to expose the tip of the pricking component while the pricking component remains disposed in the lancet body; and
- when the lancet engaging part is forced to be further moved forward, the separated lancet cap moves to the position off a pricking pathway of the pricking component within the lancet case.

The second aspect: The lancet assembly according to the first aspect, wherein the lancet engaging part has a hollow portion around a central axis of the lancet engaging part, the central axis extending along the pricking direction; and
- the lancet engaging part and the lancet are in an assembled state with each other such that the lancet is accommodated in the hollow portion of the lancet engaging part.

The third aspect: The lancet assembly according to the first or second aspect, wherein the lancet engaging part comprises a pair of cap pressing portions which are capable of making contact with a rear end portion of the lancet cap.

The fourth aspect: The lancet assembly according to any one of the first to third aspects, wherein the lancet and the lancet engaging part are accommodated within the lancet case such that the lancet and the lancet engaging part are not exposed from the lancet case.

The fifth aspect: The lancet assembly according to any one of the first to fourth aspects, wherein a slope component is provided within the lancet case, the slope component being a component for guiding the separated lancet cap to the position off the pricking pathway.

The sixth aspect: The lancet assembly according to any one of the first to fifth aspects, wherein, at a point in time before the lancet cap is separated, a forward movement of the lancet body is limited by a mutual engagement between an engagement portion "A" provided within the lancet case and an engaged portion "B" of the lancet body.

The seventh aspect: The lancet assembly according to the sixth aspect, wherein, the lancet engaging part comprises a disengagement portion for releasing the mutual engagement between the engagement portion "A" of the lancet case and the engaged portion "B" of the lancet body; and
- at a point in time after the lancet cap is separated from the lancet body, the disengagement portion of the lancet engaging part, when being forced to be moved forward, presses and outwardly displaces the engagement portion "A", and thereby the mutual engagement between the engagement portion "A" and the engaged portion "B" is finally released.

The eighth aspect: The lancet assembly according to any one of the first to the seventh aspects, wherein a partial cutout is provided in a body of the lancet case, whereas the lancet engaging part has an indicator portion; and
- when the lancet engaging part is forced to be moved forward until the separated lancet cap is positioned off the pricking pathway, the indicator portion of the lancet engaging part becomes exposed from the partial cutout of the lancet case.

The ninth aspect: The lancet assembly according to any one of the first to the eighth aspects, wherein a rear end portion of the lancet engaging part is capable of making contact with a forward-projecting portion provided within an injector for launching the pricking component;
- when the lancet assembly is loaded into the injector by inserting the lancet case into the injector through a front end opening of the injector, the rear end portion of the lancet engaging part abuts against the forward-projecting portion of the injector;
- when the lancet case is further inserted into the injector, a force for moving the lancet engaging part forward with respect to the lancet case is generated due to the abutment of the lancet engaging part against the forward-projecting portion of the injector, and thereby the lancet cap is pressed to be separated from the lancet body; and
- when the lancet case is furthermore inserted into the injector, the separated lancet cap moves to the position that is off the pricking pathway within the lancet case.

The tenth aspect: The lancet assembly according to the ninth aspect, wherein a rear end portion of the lancet body has an engagement portion that is capable of engaging with a plunger provided in the injector; and
- the rear end portion of the lancet body and a front end portion of the plunger make engagement with each other when the lancet assembly is loaded into the injector, and thereby the plunger is retracted as the insertion of the lancet case advances so that a force required for launching the pricking component is stored in the plunger.

The eleventh aspect: The lancet assembly according to any one of the first to the tenth aspects, wherein the lancet engaging part comprises a flexible locking portion, whereas the lancet body comprises a recess portion; and when the lancet engaging part is forced to be moved forward with respect to the lancet case at a point in time after the launch of the pricking component, the flexible locking portion of the lancet engaging part abuts against an inner-wall raised portion of the lancet case, and thereby the flexible locking portion is displaced inwardly so that at least one part of the flexible locking portion is located in the recess portion of the lancet body.

The twelfth aspect: The lancet assembly according to any one of the first to the eleventh aspects, wherein an injector for launching the pricking component, the injector being to be used in combination with the lancet assembly according to any one of the first to eleventh aspects, comprising:
- a plunger which is capable of engaging with a rear end portion of the lancet body and causing a launch of the lancet body in a pricking direction;
- a cylindrical lancet assembly receiving part which is provided at a front end opening of the injector and includes therein a forward-projecting portion; and
- a trigger lever for triggering the launch of the pricking component when being pressed from the outside for the pricking,
- wherein the injector is configured to allow a lancet assembly to be loaded into the injector such that a part of the lancet case is accommodated in the lancet assembly receiving part of the injector; and
- wherein, when the lancet assembly with a forward movement of the lancet body being limited is loaded into the injector, the lancet engaging part abuts against the forward-projecting portion of the lancet assembly receiving part, and when the lancet case is further forced to be inserted, a force for moving the lancet engaging part forward with respect to the lancet case is applied to the lancet engaging part due to the abutment of the lancet engaging part with the forward-projecting portion of the lancet assembly receiving part, and thereby the lancet cap is separated from the lancet body and the separated lancet cap moves to a position off the pricking pathway.

The thirteenth aspect: The injector according to the twelfth aspect, further comprising a case locking part on a front sided-inner wall of a housing of the injector,
- wherein a surface of the case locking part is provided with a stopper projecting toward the inside of the injector, and a spring is provided between the case locking part and a sidewall of the housing of the injector so that an inward force toward the inside of the injector is applied to the case locking part; and
- when the lancet assembly is loaded into the injector, a locking projection provided on an outer wall surface of the lancet case slides on the case locking part, and after the sliding locking projection of the lancet case rides over the stopper, the locking projection and the stopper become capable of engaging with each other so that the loaded lancet case cannot come off the injector.

The fourteenth aspect: The injector according to the twelfth or thirteenth aspect, further comprising an ejector for ejecting the loaded lancet assembly from the injector,
- a forward movement of the ejector after the pricking forces the lancet engaging part to be moved forward within the lancet case due to an abutment of the ejector against the rear end portion of the lancet engaging part, and thereby a front end of the lancet engaging part pushes against an inner wall of the lancet case; and
- a further forward movement of the ejector generates a force for forward pushing the whole of the lancet assembly so that the lancet assembly is ejected from the injector.

The fifteenth aspect: The injector according to the fourteenth aspect, wherein the ejector has an elongate shape as a whole, and a rear end portion of the elongate ejector is provided with a force point to be used for a forward movement of the ejector; and
- the force point of the ejector is exposed from a housing of the injector.

The sixteenth aspect: The injector according to the fourteenth or fifteenth aspect when appendant to the eleventh aspect, wherein,
- when the lancet engaging part is pushed by the ejector to be moved forward with respect to the lancet case within the lancet case, the flexible locking portion of the lancet engaging part abuts against an inner-wall raised portion of the lancet case so that the flexible locking portion is inwardly displaced, and thereby at least one part of the flexible locking portion is located in the recess portion of the lancet body.

The seventeenth aspect: The injector according to any one of the fourteenth to sixteenth aspects when appendant to the eighth aspect, wherein,
- when the lancet engaging part is pushed by the ejector to be moved forward within the lancet case at a point in time after the launch of the pricking component, the indicator portion of the lancet engaging part is furthermore exposed from the partial cutout of the lancet case.

The eighteenth aspect: The injector according to any one of the fourteenth to seventeenth aspects when appendant to the thirteenth aspect, wherein the ejector comprises an unlocking portion having such an elongate form that it projects forward; and
- when the ejector is forced to be moved forward after the pricking, the unlocking portion of the ejector abuts against the case locking part, and thereby forcing the case locking part to be moved outwardly so that the locking projection and the stopper are no longer capable of engaging with each other.

The nineteenth aspect: The pricking device comprises the lancet assembly according to any one of the first to eleventh aspects, and the injector according to any one of the twelfth to eighteenth aspects.

Although some embodiments of the present invention have been hereinbefore described, such embodiments are only for illustrative purpose as typical examples, and thus the present invention is not limited to these embodiments. It will be readily appreciated by those skilled in the art that various modifications are possible without departing from the scope of the invention. For example, the following modified embodiments are possible.

In the accompanying drawings, the pricking component 153 has a "needle form" whose uppermost portion is wholly sharpened, but is not necessarily limited thereto. For example, the pricking component 153 may have a "blade form" with only one side face of its tip sharpened.

Further, as for the lancet 150, the bridging component 154 of the lancet 150 may be cut off in advance. Furthermore, no bridging component 154 may be also provided in the lancet 150. That is, instead of the case where the lancet cap 152 and the lancet body 151 are interconnected via the bridging component 154, the lancet cap 152 and the lancet body 151 may be formed separately (i.e., the lancet cap 152 and the lancet body 151 are not in an interconnected form). In case where no bridging component 154 is provided in the lancet 150, the lancet assembly 100 of the present invention has the following configuration and function:

The lancet assembly 100 comprises a lancet 150, a lancet engaging part 190 and a lancet case 102 housing the lancet and the lancet engaging part, wherein the lancet 150 comprises a lancet body 151, a lancet cap 152 and a pricking component 153, the lancet body 151 and the lancet cap 152 being made of resin and the pricking component being made of metal, the pricking component 153 is disposed in both the lancet body 151 and the lancet cap 152, the tip of the pricking component 153 is covered with the lancet cap 152; and wherein the lancet engaging part 190 and the lancet cap are disposed such that they are capable of making contact with each other;

when the lancet engaging part 190 is forced to be moved forward with respect to the lancet 150 in a pricking direction, the lancet cap 152 is pressed by the lancet engaging part 190, and the lancet body 151 and the lancet cap 152 are forced to be moved away from each other so that the lancet cap 152 is separated from the pricking component 153 to expose the tip of the pricking component 153 while the pricking component 153 remains disposed in the lancet body 151; and when the lancet engaging part 190 is forced to be further moved forward, the separated lancet cap 152 moves to the position off a pricking pathway of the pricking component 153 within the lancet case 102.

Those skilled in the art will understand that this lancet assembly also has similar features and functions to those of the lancet assembly described previously.

Industrial Applicability

The pricking device composed of the lancet assembly and the injector as described above makes it easier and safer to take a sample of the blood. The pricking device is not limited to taking the blood sample of diabetic, and can also be used in various applications requiring blood samples.

CROSS REFERENCE TO RELATED PATENT APPLICATION

The present application claims the rights of priority of Japanese Patent Application No. 2011-278465 (filed on Dec. 20, 2011, the title of the invention: "LANCET ASSEMBLY AND PRICKING DEVICE"), the disclosures of which are all incorporated herein by reference.

Reference Numerals

100 . . . Lancet assembly, 102 . . . Lancet case, 104 . . . Projection provided on outer surface of lancet case, 103 . . . Rear opening end, 105 . . . Pricking opening, 106 . . . Partial cutout of housing case, 107 . . . Projection provided on inner wall of case, 110 . . . Engagement portion "A" provided within case, 111 . . . Projection of engagement portion "A", 114 . . . Elongated section of engagement portion "A", 135 . . . Engaged portion "B" provided in lancet body, 150 . . . Lancet, 151 . . . Lancet body, 152 . . . Lancet cap, 152b . . . Sloping face of cap, 153 . . . Pricking component, 153a . . . Tip of pricking component, 154 . . . Bridging component, 157 . . . guided component of lancet body, 158 . . . Recess portion of lancet body, 165 . . . Rear end portion of lancet body, 165' . . . Transverse raised extension provided at rear end portion of lancet body, 170 . . . Slope component provided within case, 170a . . . Sloping face of slope component, 180 . . . Raised portion (internal raised portion) provided within case, 190 . . . Lancet engaging part, 191 . . . Guide of lancet engaging part, 192 . . . Cap pressing portion of lancet engaging part, 193 . . . Front end portion of lancet engaging part, 194 . . . Disengagement portion of lancet engaging part, 195 . . . Indicator portion of lancet engaging part, 196 . . . Flexible locking portion of lancet engaging part, 197 . . . Hollow portion of lancet engaging part, 198a to 198d . . . Projections of lancet engaging part, 199,199' . . . Rear end portion of lancet engaging part, 200 . . . Injector, 202 . . . Front end opening of injector, 201(201a, 201b) . . . Housing of injector, 204 . . . Plunger, 204a . . . Front end portion of plunger, 204b . . . Trigger projection of plunger, 204c . . . Rear end portion of plunger, 205a . . . Fire spring, 205b . . . Return spring, 210 . . . Lancet assembly receiving part, 212 . . . Forward projecting portion of lancet assembly receiving part, 217 . . . Guiding projection of lancet assembly receiving part, 230 . . . Trigger lever, 230a . . . Rear stepped portion of trigger lever, 230c . . . Trigger ring, 240 . . . Case locking part, 240a . . . Stopper, 240b . . . Rear end edge of locking part, 242 . . . Spring used for case locking, 250 . . . Hook, 270 . . . Ejector, 272 . . . Force point provided at rear end portion of ejector, 272a . . . Partial cutout provided at rear end portion of ejector, 274 . . . Front end portion of ejector (pressing portion capable of making contact with lancet engaging portion), 274a . . . Wing provided at forward end portion of ejector, 275 . . . Unlocking portion of ejector, 275a . . . Tip of Unlocking portion, 300 . . . Adjuster (pricking depth adjustment part), 310 . . . Adjuster ring, 320 . . . Adjuster spring, and 1000 . . . Pricking device.

The invention claimed is:

1. A lancet assembly comprising:

a lancet;

a lancet engaging part; and a lancet case housing the lancet and the lancet engaging part;

wherein the lancet comprises a lancet body, a lancet cap, and a pricking component, the lancet body and the lancet cap being made of resin and the pricking component being made of metal, the pricking component being disposed in both the lancet body and the lancet cap, the tip of the pricking component being covered with the lancet cap, and the lancet cap and the lancet body being integrally connected together by a bridging component;

wherein the lancet engaging part and the lancet cap are configured to make contact with each other;

wherein the lancet and the lancet engaging part are configured such that, when the lancet engaging part is forced to be moved forward with respect to the lancet in a pricking direction, the lancet cap is pressed by the lancet engaging part such that the bridging component is broken so that the lancet cap is separated from the lancet body to expose the tip of the pricking component while the pricking component remains disposed in the lancet body;

wherein the lancet, the lancet engaging part, and the lancet case are configured such that, when the lancet engaging part is forced to be further moved forward after the bridging component is broken, the separated lancet cap moves to the position off a pricking pathway of the pricking component within the lancet case;

wherein the lancet and the lancet case are configured such that, before the bridging component is broken and the lancet cap is separated from the lancet body, a forward movement of the lancet body is inhibited by engagement between an engagement portion of the lancet case and an engaged portion of the lancet body;

wherein the lancet engaging part comprises a disengagement portion for releasing the engagement between the engagement portion of the lancet case and the engaged portion of the lancet body;

wherein the lancet, the lancet engaging part, and the lancet case are configured such that, after the bridging component is broken and the lancet cap is separated from the lancet body, forward movement of the disengagement portion of the lancet engaging part presses and outwardly displaces the engagement portion of the lancet case to release the engagement between the engagement portion of the lancet case and the engaged portion of the lancet body;

wherein the lancet engaging part comprises a flexible locking portion, and the lancet body comprises a recess portion; and wherein the lancet, the lancet engaging part, and the lancet case are configured such that, when the lancet engaging part is forced to be moved forward with respect to the lancet case after launch of the pricking component, the flexible locking portion of the lancet engaging part abuts against an inner-wall raised portion of the lancet case to displace the flexible locking portion inwardly so that at least one part of the flexible locking portion is located in the recess portion of the lancet body so as to lock the lancet to the lancet case.

2. The lancet assembly according to claim 1, wherein the lancet engaging part is configured to have a hollow portion around its central axis extending along the pricking direction; and the lancet engaging part and the lancet are in an assembled state with each other such that the lancet is positioned in the hollow portion of the lancet engaging part.

3. The lancet assembly according to claim 1, wherein the lancet engaging part comprises a pair of cap pressing portions which are configured to make contact with a rear end portion of the lancet cap.

4. The lancet assembly according to claim 1, wherein the lancet and the lancet engaging part are accommodated within the lancet case such that the lancet and the lancet engaging part are not exposed from the lancet case.

5. The lancet assembly according to claim 1, wherein a slope component is provided within the lancet case, the slope component being configured to guide the separated lancet cap to the position off the pricking pathway.

6. The lancet assembly according to claim 1, wherein a partial cutout is provided in a body of the lancet case, and the lancet engaging part has an indicator portion; and wherein the lancet case and the lancet engaging part are configured such that, when the lancet engaging part is forced to be moved forward until the separated lancet cap is positioned off the pricking pathway, the indicator portion of the lancet engaging part is exposed from the partial cutout of the lancet case.

7. A pricking device comprising:
the lancet assembly according to claim 1; and
an injector for launching the pricking component of the lancet assembly;

wherein a rear end portion of the lancet engaging part is configured to make contact with a forward-projecting portion provided within the injector to be engaged with the lancet assembly for launching the pricking component of the lancet assembly;

wherein the lancet, the lancet engaging part, and the lancet case are configured such that:
when the lancet assembly is loaded into the injector by inserting the lancet case into the injector through a front end opening of the injector, the rear end portion of the lancet engaging part abuts against the forward-projecting portion of the injector;
when the lancet case is further inserted into the injector, a force for moving the lancet engaging part forward with respect to the lancet case is generated due to the abutment of the lancet engaging part against the forward-projecting portion, and thereby the lancet cap is pressed to be separated from the lancet body; and
when the lancet case is furthermore inserted into the injector, the separated lancet cap moves to the position that is off the pricking pathway within the lancet case.

8. The pricking device according to claim 7, wherein a rear end portion of the lancet body has an engagement portion configured to engage with a plunger provided in the injector; and wherein the lancet and the lancet case are configured such that the rear end portion of the lancet body and a front end portion of the plunger engage with each other when the lancet assembly is loaded into the injector, and thereby the plunger is retracted with the insertion of the lancet case so that a force required for launching the pricking component is stored in the plunger.

9. A pricking device comprising:
the lancet assembly according to claim 1; and
an injector for launching the pricking component of the lancet assembly;
wherein the injector of the pricking device includes:
a plunger configured to engage with a rear end portion of the lancet body and to cause a launch of the lancet body in a pricking direction;
a cylindrical lancet assembly receiving part which is provided at a front end opening of the injector and includes therein a forward-projecting portion; and
a trigger lever for triggering the launch of the pricking component when being pressed from the outside for the pricking,
wherein the injector is configured to allow the lancet assembly to be loaded into the injector such that a part of the lancet case is accommodated in the lancet assembly receiving part of the injector; and
wherein the lancet assembly and the injector are configured such that, when the lancet assembly with a forward movement of the lancet body being inhibited is loaded into the injector, the lancet engaging part abuts against the forward-projecting portion of the lancet assembly receiving part, and when the lancet case is further forced to be inserted, a force for moving the lancet engaging part forward with respect to the lancet case is applied to the lancet engaging part due to the abutment of the lancet engaging part with the forward-projecting portion, and thereby the lancet cap is separated from the lancet body and the separated lancet cap moves to a position off the pricking pathway.

10. The pricking device according to claim 9, wherein the injector further has a case locking part on a front sided-inner wall of a housing of the injector, wherein a surface of the case locking part is provided with a stopper projecting toward the inside of the injector, and a spring is provided between the case locking part and a sidewall of the housing of the injector so that an inward force toward the inside of the injector is applied to the case locking part; and wherein the injector and lancet assembly are configured such that, when the lancet assembly is loaded into the injector, a locking projection provided on an outer wall surface of the lancet case slides on the case locking part, and after the sliding locking projection of the lancet case rides over the stopper, the locking projection and the stopper become capable of engaging with each other so that the loaded lancet case cannot come off the injector.

11. The pricking device according to claim 9, wherein the injector further includes an ejector for ejecting the loaded lancet assembly from the injector, and wherein the injector and the lancet assembly are configured such that:
- a forward movement of the ejector after the pricking forces the lancet engaging part to be moved forward within the lancet case due to an abutment of the ejector against the rear end portion of the lancet engaging part, and thereby a front end of the lancet engaging part pushes against an inner wall of the lancet case; and
- a further forward movement of the ejector generates a force for forward pushing the entire lancet assembly so that the lancet assembly is ejected from the injector.

12. The pricking device according to claim 11, wherein the ejector has an elongate shape, and a rear end portion of the elongate ejector is provided with a force point to be used for a forward movement of the ejector; and the force point of the ejector is exposed from a housing of the injector.

13. The pricking device according to claim 11, wherein a partial cutout is provided in a body of the lancet case, and the lancet engaging part is provided with an indicator portion; and at a point in time after the lancet engaging part is forced to be moved forward to such a position that the separated lancet cap is positioned off the pricking pathway, the indicator portion of the lancet engaging part is exposed from the partial cutout of the lancet case; and when the lancet engaging part is pushed by the ejector to be moved forward with respect to the lancet case at a point in time after the launch of the pricking component, the indicator portion of the lancet engaging part is furthermore exposed from the partial cutout of the lancet case.

14. The pricking device according to claim 11, further comprising a case locking part on a front sided-inner wall of a housing of the injector, and an unlocking portion having such an elongate form that the unlocking portion projects forward, a surface of the case locking part is provided with a stopper projecting toward the inside of the injector, and a spring is provided between the case locking part and a sidewall of a housing of the injector so that an inward force toward the inside of the injector is applied to the case locking part;

wherein the injector and the lancet assembly are configured such that:
- when the lancet assembly is loaded into the injector, a locking projection provided on an outer wall surface of the lancet case slides on the case locking part, and after the sliding locking projection of the lancet case rides over the stopper, the locking projection and the stopper are configured to engage with each other so that the loaded lancet case cannot come off the injector; and
- when the ejector is forced to be moved forward after the pricking, the unlocking portion of the ejector abuts against the case locking part such that the case locking part is moved outwardly so that the locking projection and the stopper are no longer configured to engage with each other.

* * * * *